(12) United States Patent
Seuntjens et al.

(10) Patent No.: US 10,413,754 B2
(45) Date of Patent: *Sep. 17, 2019

(54) METHOD AND SYSTEM FOR CALORIMETRY PROBE

(71) Applicant: Sun Nuclear Corporation, Melbourne, FL (US)

(72) Inventors: Jan Seuntjens, Montreal (CA); Arman Sarfehnia, Toronto (CA); James Renaud, Montreal (CA)

(73) Assignee: Sun Nuclear Corporation, Melbourne, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/932,363

(22) Filed: Feb. 16, 2018

(65) Prior Publication Data

US 2018/0250529 A1 Sep. 6, 2018

Related U.S. Application Data

(63) Continuation of application No. 15/448,483, filed on Mar. 2, 2017, now Pat. No. 9,895,557, which is a (Continued)

(51) Int. Cl.
*A61N 5/10* (2006.01)
*G01T 1/12* (2006.01)
*G01K 17/00* (2006.01)

(52) U.S. Cl.
CPC ......... *A61N 5/1071* (2013.01); *A61N 5/1075* (2013.01); *G01K 17/003* (2013.01); *G01T 1/12* (2013.01); *A61N 2005/1076* (2013.01)

(58) Field of Classification Search
CPC ................ A61N 5/1071; A61N 5/1075; A61N 2005/1076; G01K 17/003; G01T 1/12
See application file for complete search history.

(56) References Cited

U.S. PATENT DOCUMENTS 759,608 A 5/1904 Harper
1,239,145 A 9/1917 Wantz
(Continued)

FOREIGN PATENT DOCUMENTS

CA 2718408 9/2009
DE 102009039345 A1 3/2011
(Continued)

OTHER PUBLICATIONS

McEwen et al., A portable calorimeter for measuring absorbed dose in the radiotherapy clinic., Dec. 2000, Phys. MEd. Biol., vol. 45, pp. 3675-3691.*

(Continued)

*Primary Examiner* — Christine S. Kim
(74) *Attorney, Agent, or Firm* — Pillsbury Winthrop Shaw Pittman LLP

(57) ABSTRACT

Radiotherapy is one of the most effective treatments for cancer and its success depends critically on accurate targeting and delivery of the correct radiation dose. Accurate dosimetry is therefore essential to maintain and improve patient survival rates. However, size and long wait times currently limit water and graphite based calorimeters to standards laboratories leaving field-based dosimetry to ionization chamber measurements which depend upon a reference field-specified calibration factor. It would therefore be beneficial to provide radiotherapy equipment operators a direct approach of clinical reference dosimetry wherein the dosimeter provides increased independence on dose, dose rate, radiation energy, and energy type, etc. It would be further beneficial for such novel clinical dosimeters to be compact, function as secondary standards used routinely for measurements and allow radiotherapy doses to be measured directly and in an absolute manner. According to embodi- (Continued)

Section X-X

Section Y-Y ments of the invention novel compact graphite probe calorimeters are provided.

15 Claims, 12 Drawing Sheets

Related U.S. Application Data continuation of application No. 14/403,416, filed as application No. PCT/CA2013/000523 on May 29, 2013, now Pat. No. 9,586,060.

(60) Provisional application No. 61/652,540, filed on May 29, 2012.

(56) References Cited

U.S. PATENT DOCUMENTS

| | | | |
|---|---|---|---|
| 2,818,510 A | 12/1957 | Verse | |
| 3,033,985 A | 5/1962 | Ben | |
| 3,394,258 A | 7/1968 | Schleiger | |
| 3,433,953 A | 3/1969 | Sweet | |
| 3,665,762 A * | 5/1972 | Domen | G01K 17/04 374/31 |
| 3,783,251 A | 1/1974 | Pavkovich | |
| 3,790,794 A | 2/1974 | Murray | |
| 3,980,885 A | 9/1976 | Steward | |
| 4,058,832 A | 11/1977 | Vagi | |
| 4,063,097 A | 12/1977 | Barrett | |
| 4,107,531 A | 8/1978 | Garratt | |
| 4,157,472 A | 6/1979 | Barrett | |
| 4,312,224 A | 1/1982 | Domen | |
| 4,450,440 A | 5/1984 | White | |
| 4,455,609 A | 6/1984 | Inamura | |
| 4,613,754 A | 9/1986 | Vinegar | |
| 4,729,099 A | 3/1988 | Iverson | |
| 4,765,749 A * | 8/1988 | Bourgade | G01K 17/003 250/352 |
| 4,777,442 A | 10/1988 | Rosenthal | |
| 4,887,287 A | 12/1989 | Cobben | |
| 5,099,505 A | 3/1992 | Seppi | |
| 5,160,337 A | 11/1992 | Cosman | |
| 5,262,649 A | 11/1993 | Antonuk | |
| 5,388,142 A | 2/1995 | Morris | |
| 5,394,452 A | 2/1995 | Swerdloff | |
| 5,596,653 A | 1/1997 | Kurokawa | |
| 5,602,892 A | 2/1997 | Llacer | |
| 5,621,214 A | 4/1997 | Sofield | |
| 5,627,367 A | 5/1997 | Sofield | |
| 5,635,709 A | 6/1997 | Sliski | |
| 5,640,436 A | 6/1997 | Kawai | |
| 5,661,310 A | 8/1997 | Jones | |
| 5,704,890 A | 1/1998 | Bliss | |
| 5,712,482 A | 1/1998 | Gaiser | |
| 5,873,826 A | 2/1999 | Gono | |
| 6,038,283 A | 3/2000 | Carol | |
| 6,125,335 A | 9/2000 | Simon | |
| 6,131,690 A | 10/2000 | Galando | |
| 6,148,272 A | 11/2000 | Bergstrom | |
| 6,175,761 B1 | 1/2001 | Frandsen | |
| 6,257,552 B1 | 7/2001 | Crow | |
| 6,261,219 B1 | 7/2001 | Meloul | |
| 6,301,329 B1 | 10/2001 | Surridge | |
| 6,345,114 B1 | 2/2002 | Mackie | |
| 6,364,529 B1 | 4/2002 | Dawson | |
| 6,398,710 B1 | 6/2002 | Ishikawa | |
| 6,516,046 B1 | 2/2003 | Froehlich | |
| 6,535,756 B1 | 3/2003 | Simon | |
| 6,552,347 B1 | 4/2003 | Dimcovski | |
| 6,560,311 B1 | 5/2003 | Shepard | |
| 6,594,336 B2 | 7/2003 | Nishizawa | |
| 6,609,626 B2 | 8/2003 | Young | |
| 6,609,826 B1 | 8/2003 | Fujii | |
| 6,626,569 B2 | 9/2003 | Reinstein | |
| 6,636,622 B2 | 10/2003 | Mackie | |
| 6,648,503 B2 * | 11/2003 | Tanaka | G01J 5/20 250/338.1 |
| 6,712,508 B2 | 3/2004 | Nilsson | |
| 6,788,759 B2 | 9/2004 | Op De Beek | |
| 6,799,068 B1 | 9/2004 | Hartmann | |
| 6,810,107 B2 | 10/2004 | Steinberg | |
| 6,810,108 B2 | 10/2004 | Clark | |
| 6,833,707 B1 * | 12/2004 | Dahn | G01N 25/4846 324/426 |
| 6,839,404 B2 | 1/2005 | Clark | |
| 6,853,702 B2 | 2/2005 | Renner | |
| 6,888,919 B2 | 5/2005 | Graf | |
| 6,904,119 B2 | 6/2005 | Oikawa | |
| 6,904,125 B2 | 6/2005 | Van Dyk | |
| 6,904,162 B2 | 6/2005 | Robar | |
| 6,974,254 B2 | 12/2005 | Paliwal | |
| 6,990,368 B2 | 1/2006 | Simon | |
| 6,992,309 B1 | 1/2006 | Petry | |
| 7,016,454 B2 | 3/2006 | Warnberg | |
| 7,065,812 B2 | 6/2006 | Newkirk | |
| 7,076,023 B2 | 7/2006 | Ghelmansarai | |
| 7,098,463 B2 | 8/2006 | Adamovics | |
| 7,116,749 B2 | 10/2006 | Besson | |
| 7,127,028 B2 | 10/2006 | Sendai | |
| 7,127,030 B2 | 10/2006 | Tamegai | |
| 7,142,634 B2 | 11/2006 | Engler | |
| 7,193,220 B1 | 3/2007 | Navarro | |
| 7,221,733 B1 | 5/2007 | Takai | |
| 7,233,688 B2 | 6/2007 | Ritt | |
| 7,234,355 B2 | 6/2007 | Dewangan | |
| 7,298,820 B2 | 11/2007 | Nelson | |
| 7,339,159 B2 | 3/2008 | Juh | |
| 7,349,523 B2 | 3/2008 | Jenkins | |
| 7,352,840 B1 | 4/2008 | Nagarkar | |
| 7,371,007 B2 | 5/2008 | Nilsson | |
| 7,386,089 B2 | 6/2008 | Endo | |
| 7,420,160 B2 | 9/2008 | Delaperriere | |
| 7,453,976 B1 | 11/2008 | Yin | |
| 7,471,765 B2 | 12/2008 | Jaffray | |
| 7,515,681 B2 | 4/2009 | Ebstein | |
| 7,579,608 B2 | 8/2009 | Takahashi | |
| 7,605,365 B2 | 10/2009 | Chen | |
| 7,668,292 B1 | 2/2010 | Bose | |
| 7,734,010 B2 | 6/2010 | Otto | |
| 7,750,311 B2 | 7/2010 | Daghighian | |
| 7,766,903 B2 | 8/2010 | Blumenkranz | |
| 7,773,723 B2 | 8/2010 | Nord | |
| 7,778,383 B2 | 8/2010 | Koehler | |
| 7,778,392 B1 | 8/2010 | Berman | |
| 7,778,680 B2 | 8/2010 | Goode, Jr. | |
| 7,782,998 B2 | 8/2010 | Langan | |
| 7,945,022 B2 | 5/2011 | Nelms | |
| 8,044,359 B2 | 10/2011 | Simon | |
| 8,093,549 B2 | 1/2012 | Navarro | |
| 8,130,905 B1 | 3/2012 | Nelms | |
| 8,136,773 B2 | 3/2012 | Schmutzer | |
| 8,147,139 B2 | 4/2012 | Papaioannou | |
| 8,218,718 B1 | 7/2012 | Van Herk | |
| 8,235,530 B2 | 8/2012 | Maad | |
| 8,242,458 B2 | 8/2012 | Rinecker | |
| 8,321,179 B2 | 11/2012 | Simon | |
| 8,325,878 B2 | 12/2012 | McNutt | |
| 8,430,564 B2 | 4/2013 | Simmons | |
| 8,457,713 B2 | 6/2013 | Kagermeier | |
| 8,474,794 B2 | 7/2013 | Liljedahl | |
| 8,536,547 B2 | 9/2013 | Maurer | |
| 8,541,756 B1 | 9/2013 | Treas | |
| 8,605,857 B1 | 12/2013 | Renner | |
| 8,632,448 B1 | 1/2014 | Schulte | |
| 8,726,814 B1 | 5/2014 | Matteo | |
| 8,794,899 B2 | 8/2014 | Cozza | |
| 8,833,709 B2 | 9/2014 | Weng | |
| 8,840,304 B2 | 9/2014 | Perez Zarate | |
| 8,840,340 B2 | 9/2014 | Eisenhower | |
| 8,874,385 B2 | 10/2014 | Takayanagi | |
| 8,927,921 B1 | 1/2015 | Nelms | |
| 9,050,460 B2 | 6/2015 | Hildreth | |
| 9,097,384 B1 | 8/2015 | Simon | |
| 9,463,336 B2 | 10/2016 | Nelms | |

(56) References Cited

U.S. PATENT DOCUMENTS

| | | | |
|---|---|---|---|
| 9,480,861 B2 | 11/2016 | Kapatoes | |
| 9,561,388 B2 | 2/2017 | Hildreth | |
| 9,586,060 B2 | 3/2017 | Seuntjens | |
| 9,750,955 B2 | 9/2017 | McNutt | |
| 9,895,557 B2 | 2/2018 | Seuntjens | |
| 2001/0042841 A1 | 11/2001 | Lyons | |
| 2002/0077545 A1 | 6/2002 | Takahashi | |
| 2002/0080912 A1 | 6/2002 | Mackie | |
| 2003/0043879 A1* | 3/2003 | Tanaka | G01K 17/00 374/31 |
| 2003/0043960 A1 | 3/2003 | Op De Beek | |
| 2003/0138077 A1 | 7/2003 | Lee | |
| 2003/0231740 A1 | 12/2003 | Paliwal | |
| 2004/0066880 A1 | 4/2004 | Oikawa | |
| 2004/0068182 A1 | 4/2004 | Misra | |
| 2004/0096033 A1 | 5/2004 | Seppi | |
| 2004/0113094 A1 | 6/2004 | Lyons | |
| 2004/0120560 A1 | 6/2004 | Robar | |
| 2004/0211917 A1 | 10/2004 | Adamovics | |
| 2004/0228435 A1 | 11/2004 | Russell | |
| 2004/0251419 A1 | 12/2004 | Nelson | |
| 2005/0013406 A1 | 1/2005 | Dyk | |
| 2005/0077459 A1 | 4/2005 | Engler | |
| 2005/0111621 A1 | 5/2005 | Riker | |
| 2006/0002519 A1 | 1/2006 | Jenkins | |
| 2006/0033044 A1 | 2/2006 | Gentry | |
| 2006/0184124 A1 | 8/2006 | Cowan | |
| 2006/0203964 A1 | 9/2006 | Nyholm | |
| 2006/0203967 A1 | 9/2006 | Nilsson | |
| 2006/0266951 A1 | 11/2006 | Fritsch | |
| 2007/0041497 A1 | 2/2007 | Schnarr | |
| 2007/0041499 A1 | 2/2007 | Lu | |
| 2007/0071169 A1 | 3/2007 | Yeo | |
| 2007/0081629 A1 | 4/2007 | Yin | |
| 2007/0086577 A1 | 4/2007 | Kobayashi | |
| 2007/0195930 A1 | 8/2007 | Kapatoes | |
| 2008/0031406 A1 | 2/2008 | Yan | |
| 2008/0049896 A1 | 2/2008 | Kuduvalli | |
| 2008/0049898 A1 | 2/2008 | Romesberg, III | |
| 2008/0091388 A1 | 4/2008 | Failla | |
| 2008/0103834 A1 | 5/2008 | Reiner | |
| 2008/0118137 A1 | 5/2008 | Chen | |
| 2008/0260368 A1 | 10/2008 | Chang | |
| 2008/0292055 A1 | 11/2008 | Boone | |
| 2009/0003512 A1 | 1/2009 | Pouliot | |
| 2009/0067576 A1 | 3/2009 | Maltz | |
| 2009/0090870 A1* | 4/2009 | Ahnesjo | G01T 1/02 250/395 |
| 2009/0175418 A1 | 7/2009 | Sakurai | |
| 2009/0217999 A1 | 9/2009 | Becker | |
| 2009/0227841 A1 | 9/2009 | Miyako | |
| 2009/0250618 A1 | 10/2009 | Simon | |
| 2009/0252292 A1 | 10/2009 | Simon | |
| 2011/0022360 A1 | 1/2011 | Simon | |
| 2011/0051893 A1 | 3/2011 | McNutt | |
| 2011/0085716 A1 | 4/2011 | Chefd Hotel | |
| 2011/0096906 A1 | 4/2011 | Langeveld | |
| 2011/0158386 A1 | 6/2011 | Payne | |
| 2011/0210258 A1 | 9/2011 | Black | |
| 2011/0248188 A1 | 10/2011 | Brusasco | |
| 2011/0278444 A1 | 11/2011 | Navarro | |
| 2011/0306864 A1 | 12/2011 | Zarate | |
| 2012/0014618 A1 | 1/2012 | Sun | |
| 2012/0025105 A1 | 2/2012 | Brown | |
| 2012/0292517 A1 | 11/2012 | Izaguirre | |
| 2012/0305793 A1 | 12/2012 | Schiefer | |
| 2012/0326057 A1 | 12/2012 | Remeijer | |
| 2013/0048883 A1 | 2/2013 | Simon | |
| 2013/0303902 A1 | 11/2013 | Smith | |
| 2014/0073834 A1 | 3/2014 | Hildreth | |
| 2014/0094642 A1 | 4/2014 | Fuji | |
| 2014/0105355 A1 | 4/2014 | Toimela | |
| 2014/0263990 A1 | 9/2014 | Kawrykow | |
| 2015/0080634 A1 | 3/2015 | Huber | |
| 2015/0087879 A1 | 3/2015 | Nelms | |
| 2015/0124930 A1 | 5/2015 | Verhaegen | |
| 2015/0238778 A1 | 8/2015 | Hildreth | |
| 2015/0283403 A1 | 10/2015 | Kapatoes | |
| 2015/0309193 A1 | 10/2015 | Kozelka | |
| 2016/0067479 A1 | 3/2016 | Marcovecchio | |
| 2016/0166857 A1 | 6/2016 | Nelms | |
| 2016/0310762 A1 | 10/2016 | Ramezanzadeh Moghadam | |
| 2017/0021194 A1 | 1/2017 | Nelms | |
| 2018/0185672 A1 | 7/2018 | Ramezanzadeh Moghadam | |

FOREIGN PATENT DOCUMENTS

| | | |
|---|---|---|
| EP | 1060726 | 12/2000 |
| EP | 1060726 B1 | 6/2004 |
| EP | 2016445 | 1/2009 |
| EP | 2078537 A1 | 7/2009 |
| EP | 2117649 A2 | 11/2009 |
| EP | 2186542 | 5/2010 |
| EP | 2457237 | 5/2012 |
| EP | 2708919 A2 | 3/2014 |
| EP | 2865417 | 4/2015 |
| EP | 2904974 | 8/2015 |
| EP | 3074088 | 10/2016 |
| EP | 3075417 | 10/2016 |
| JP | 05154209 | 6/1993 |
| JP | 2003310590 A | 11/2003 |
| JP | 2008105982 | 5/2008 |
| JP | 2010215428 | 9/2010 |
| JP | 2010234521 | 10/2010 |
| WO | 2006138513 | 12/2006 |
| WO | 2008013956 | 1/2008 |
| WO | 2009114669 | 9/2009 |
| WO | 2009120494 | 10/2009 |
| WO | 2009137794 | 11/2009 |
| WO | 2011011471 | 1/2011 |
| WO | 2012053440 | 4/2012 |
| WO | 2013049839 | 4/2013 |
| WO | 2013177677 | 12/2013 |
| WO | 2015024360 | 2/2015 |
| WO | 2015073899 | 5/2015 |
| WO | 2016172352 | 10/2016 |

OTHER PUBLICATIONS

Linacre, J.k., Harwell Graphite Calorimeter, 1970, IAEA, vol. 47, pp. 47-54.*

"HI-ART,"; www.tomotherapy.com; TomoTherapy, Madison, WI; 2007; pp. 1-8.

"RAPID ARC"; Varian Medical Systems, Inc., Palo Alto, CA; www.varian.com; 2007; pp. 1-8.

"VMAT"; Elekta,Ltd., Crawley UK; Document No. 4513 3710770; Oct. 8, 2008.

"Waterphantom Dosimetry"; Medical Physics, vol. 3, May/Jun. 1976; pp. 189.

Ahnesjo et al. Phys. Med. Biol. 44, R99-R155 1999.

Ahnesjo et al., Acta. Oncol., 26, 49-56, 1987.

Ahnesjo, Med. Phys. 16, 577-92, 1989.

Albers et al., CRC HAndbook of Chemistry and Physics, 87th Ed., Edited by R.C. Weast (CRC, Cleveland, 1976. pp. F-11, D-171, E-6.

Almond et al. In "AAPM TG-51 Protocol for Clinical Reference Dosimetry of Hign Energy Photon and Electron Beams" (Med. Phys. VI, 26, pp. 1847-1870, 1999.

Amanatides et al., Eurographics '87, Conference Proceedings, 1987.

Aspen Aerogels, Pyrogel.RTM. 2250 Datasheet (Aspen Aerogels, Inc., Northborough, 2010).

Benedick Fraass; "Quality Assurance for Clinical Radiotherapy Treatment Planning," Med Phys., 25(10), Oct. 1998; pp. 1773-1829.

Berlyand et al., "Portable Calorimeter for Measuring Absorbed Doses of X-Rays and Electrons from Accelerators", translated from Izeritel'naya Teknika, No. 11, Nov. 1991, pp. 56-58.

Boutillon in "Gap Correction for the Calorimetric Measurement of Absorbed Dose in Graphite with a 60Co Beam" (Phys. Med. Biol., vol. 34, pp. 1809-1821, 1989.

Brusasco, C, et al. 'A Dosimetry System for Fast Measurement of 3D Depth-dose Profiles in Charged-particle Tumor Therapy with

(56) References Cited

OTHER PUBLICATIONS

Scanning Techniques.' Nuclear Instruments & Methods in Physics Research, Section—B: Beam Interactions With Materials and Atom 168.4 (2000): 578-92.

Cyberknife; Cyberknife Systems; "The Standard of Radiosurgery" by Accuracy, Sunnyvale, CA; 2009; pp. 1-6.

D.W.O. Rogers; "Montey Carlo Techniques in Radiotherapy,"; Physics in Canada, Medical Physics Special Issue, v. 58 #2; 2002; pp. 63-70.

Daures et al., "New Constant-Temperature Operating Mode for Graphite Calorimeter at LNE-LNHB", Physics in Medicine and Biology, vol. 50, 2005, No. pp. 4035-4052.

Daures et al., "Small section graphite calorimeter (CR10) at LNE-LNHB for measurement in small beams for IMRT", Metrologica, (20111201), XP020229547.

Daures et al., "Small Section Graphite Calorimeter (GR-10) at LNE-LNHB for Measurements in Small Beams for IMRT Metrologia", vol. 49, No. 5, 2012, pp. S174-S178.

Domen et al., "A Heat-loss-Compensated Calori meter: Theory, Design, and Performance", Journal of Research of the National Bureau of Standards—A. Physics and Chemistry, vol. 78A, No. 5, Sep.-Oct. 1974, pp. 595-610.

Domen, "Absorbed Dose Water Calorimeter" (Med. Phys., vol. 7, pp. 157-159).

Duane et al., "An Absorbed Dose Calorimeter for IMRT Dosimetry", Metrologia, vol. 49, No. 5, 2012, pp. S168-S173.

EP2277353 Search Report dated Jul. 21, 2017.

EP2457237 Supplemental European Search Report and Written Opinion dated Mar. 8, 2017.

G.J. Kutcher; "Comprehensive AQ for Radiation Oncology Report;" AAPM Radiation Therapy Committee Task Group 40; Med. Phys., 21; Apr. 1994; pp. 581-618.

Iaea, TRS., "398. Absorbed Dose Determination in External Beam Radiotherapy: An International Code of Practice for Dosimetry based on Standards of Absorbed Dose to Water," Vienna International Atomic Energy Agency (2000).

Indra J. Das, Chee-Wai Cheng, Ronald J. Watt, Anders Ahnesjo, John Gibbons, X. Allen Li, Jessica Lowenstien, Raj K. Mitra, William E. Simon, Timothy C. Zhu; Accelerator Beam Data Commissioning Equiptment and Procedures; Report of the TG-106 of the Therapy Physics Committee of the AAPM; Med. Phys. 35(9), Sep. 2008; pp. 4186-4215.

J. Seuntjens and S. Duane, "Photon absorbed dose standards," Metrologia 46, S39-S58 (2009).

Joseph O. Deasy; "A Computational Environment for Radiotherapy Research," Med. Phys. 30, (5), May 2003; pp. 979-985.

Kawrakow et al. In "The EGSnrc Code System: Monte-Carlo Simulation of Electron and Photon Transport" (Canadian National Research Center, NRC Report PIRS-701, 2006.

Liu et al., Med. Phys. 24, 1729-1741, 1997.

Lu et al., Phys. Med. Biol. 50, 655-680, 2005.

Mackie et al., Med. Phys. 12, 188-196, 1985.

Mackie et al., Phys. Med. Biol. 33, 1-20, 1988.

Mackie et al., Use of Comp. In Rad. Ther., 107-110 1987.

MapCALC; www.sunnuclear.com; manufactured by Sun Nuclear Corp.; Melbourne, FL; 2009.

MapCheck and EPIDose; www.sunnuclear.com; manufactured by Sun Nuclear Corp.; Melbourne,FL; 2010.

Mathilda Van Zijtveld, Maaretn L.P. Dirkxa, Hans C.J. De Boera, and Ben J.M. Heijmen; "3D Dose Reconstruction for Clinical Evaluation of IMRT Pretreatment Verification with an EPID." Radiotherapy and Oncology, 82(2); Feb. 2007; pp. 201-201.

McDonald et al., "Portable Tissue Equivalent Calorimeter", Medical Physics, vol. 3, 2, Mar.-Apr. 1976, pp. 80-86.

McEwen et al., Portable Graphite Calorimeter for Measuring Absorbed Dose in the Radiotherapy Clinic.Standards and Codes of Practice in Medical Radiation Dosimetry,IAEA-CN-96-9P,2002, pp. 115-121.

Miller, "Polystyrene Calorimeter for Electron Beam Dose Measurements", Radiation Physics Chemistry vol. 46, No. 4-6, Aug. 1995, pp. 1243-1246.

Mohan et al., Med. Phys. 12, 592-597, 1985.

Myers et al., "Precision Adiabatic Gamma-Ray Calorimeter using Thermistor Thermometry", Review of Scientific Instruments, vol. 32, No. 9, Sep. 1961, pp. 1013-1015.

Nelms, Benjamin. "Variation in External Beam Treatment, Plan Quality: An Inter-institutional Study of Planners and Planning Systems." Practical Radiation Oncology 2.4 (2012): 296-305.

Nutbrown et. "Evaluation of Factors to Convert Absorbed Dose Calibrations in Graphite to Water for Mega-Voltage Photon Beams" (UK National Pysical Laboratory, NPL Report CIRM 37, 2000.

Ostrowsky et al., "The Construction of the Graphite Calorimeter GR9 at LNE-LNHB (Geometrical and technical considerations)", Report CEA-R-6184, 2008, 52 pages.

Otto, Med. Phys. 35, 310-317, 2008.

Owen et al "Correction for the Effect of the Gaps around the Core of an Absorbed Dose Graphite Calorimeter in High Energy Photon Radiation" (Phys. Med. Biol., vol. 36, pp. 1699-1704, 1991.

Palmans et al., "A Small-Body Portable Graphite Calorimeter for Dosimetry in Low-Energy Clinical Proton Beams", Physics in Medicine and Biology, vol. 49, No. 16, Aug. 2004, pp. 3737-3749.

Papanikolaou et al., Med. Phys. 20, 1327-1336, 1993.

PCT App. No. PCT/US2009/036775; International Preliminary Report on Patentability Chapter II and Written Opinion dated Sep. 12, 2010.

PCT App. No. PCT/US2009/036775; International Search Report dated Nov. 12, 2009.

PCT App. No. PCT/US2009/036917; International Preliminary Report on Chapter II Patentability dated Mar. 15, 2011.

PCT App. No. PCT/US2009/036917; International Search Report dated Sep. 17, 2009.

PCT App. No. PCT/US2009/036917; Written Opinion dated Sep. 12, 2010.

PCT App. No. PCT/US2009/043341; International Preliminary Report on Patentability Chapter I dated Nov. 9, 2010.

PCT App. No. PCT/US2009/043341; International Search Report dated Jan. 5, 2010.

PCT App. No. PCT/US2009/043341; Written Opinion of the International Search Authority dated Nov. 8, 2010.

PCT App. No. PCT/US2010/042680; International Preliminary Report on Patentability Chapter I dated Jan. 24, 2012.

PCT App. No. PCT/US2010/042680; International Search Report dated Jan. 27, 2011.

PCT App. No. PCT/US2010/042680; International Written Opinion dated Jan. 23, 2012.

PCT App. No. PCT/US2012/053440; International Preliminary Report on Patentability Chapter I dated Mar. 3, 2015.

PCT App. No. PCT/US2012/053440; International Search Report and Written Opinion dated Mar. 26, 2014.

PCT App. No. PCT/US2012/058345; International Preliminary Report on Patentability Chapter I dated Apr. 1, 2014.

PCT App. No. PCT/US2012/058345; International Search Report dated Apr. 17, 2013.

PCT App. No. PCT/US2012/058345; International Written Opinion of the International Search Authority dated Mar. 29, 2014.

PCT App. No. PCT/US2014/065808; International Preliminary Report on Patentability Chapter I dated May 17, 2016.

PCT App. No. PCT/US2014/065808; International Search Report and Written Opinion dated May 21, 2015.

PCT App. No. PCT/US2015/024360; International Preliminary Report on Patentability Chapter I dated Oct. 4, 2016.

PCT App. No. PCT/US2015/024360; International Search Report and Written Opinion dated Oct. 8, 2015.

PCT App. No. PCT/US2016/028664; International Preliminary Report on Patentability dated Nov. 2, 2017.

PCT App. No. PCT/US2017/062608; International Search Report and Written Opinion dated Feb. 22, 2018.

PCT/US2017/044472; International Search Report and Written Opinion of the International Searching Authority, or the Declaration dated Oct. 13, 2017.

Petree et al., "A Comparison of Absorbed Dose Determinations in Graphite by Cavity Ionization Measurements and by Calorimetry",

(56) References Cited

OTHER PUBLICATIONS

Journal of Research of the National Bureau of Standards—C. Engineering and Instrumentation. vol. 71 C, No. 1, Jan.- Mar. 1967, pp. 19-27.
Picard et al., "Construction of an Absorbed-Dose Graphite Calorimeter", Report BIPM-09/01' May 2009, 12 pages.
R. Alfonso et al., 'A new formalism for reference dosimetry of small and nonstandard fields,' Med. Phys. 35, 5179-5186 (2008).
Renaud et al., "Development of a graphite probe calorimeter for absolute clinical dosimetry", MED. PHVS., (20130109), vol. 40, No. 2, p. 020701, XP012170941.
Robert M. Eisberg; "Fundamentals of Modern Physics," Chapter 9—Perturbation Theory; John Wiley & Sons; 1967; pp. 268-272.
Rogers, "The physics of AAPM's TG-51 protocol," in Clinical Dosimetry Measurements in Radiotherapy, Medical Physics Monograph No. 34, edited by D. W. O. Rogers and J. E. Cygler (Medical Physics Publishing, Madison, WI, 2009), pp. 239-298.
Ross et al. In "Water Calorimetry for Radiation Dosimetry" (Phys. Med. Biol., vol. 41, pp. I-29).
S. Picard, D. T. Burns, and P. Roger, "Determination of the specific heat capacity of a graphite sample using absolute and differential methods," Metrologia 44, 294-302 (2007).
Sander et al., "NPL's new absorbed dose standard for the calibration of HDR 192Ir brachytherapy sources," Metrologia 49, S184-S188 (2012).
Seuntjens et al., Review of Calorimeter Based Absorbed Dose to Water Standards, Standards and Codes of Practice in Medical Radiation Dosimetry, IAEA-CN-96-3,2002 p. 37-66.
Stewart in "The Development of New Devices for Accurate Radiation Dose Measurement: A garded Liquid Ionization Chamber and an Electron Sealed Water Calorimeter" (Ph. D. Dissertation McGill University, 2007, pp. 1-170.
Stewart in "The Development of New Devices for Accurate Radiation Dose Measurement: A garded Liquid Ionization Chamber and an Electron Sealed Water Calorimeter" (Ph. D. Dissertation McGill University, 2007, pp. 171-240.
T.R. Mcnutt, T.R. Mackie, P.J. Reckwerdt, B.R. Paliwal; "Analysis and Convergence of the Iterative Convolution/Superposition Dose Reconstruction Technique,"; Med. Phys. 24(9) Sep. 1997; pp. 1465-1476.
Williams, SIGGRAPH Comput. Graph. 17, 3, 1-11, 1983.
Witzani et al., "A Graphite Absorbed-Dose Calorimeter in the Quasi-Isothermal Mode of Operation", Metrologia, vol. 20, No. 3, 1984, pp. 73-79.
Sundara et al., "Graphite Calorimeter in Water and Calibration of Ionization Chambers in Dose to Water for 60Co Gamma Radiation", Medical Physics, vol. 7, No. 3, May-Jun. 1980, pp. 196-201.
Yan et al., Phys. Med. Biol. 42, 123-132, 1997.
Yu, Phys. Med. Biol. 40, 1435-1449, 1995.
McEwen et al.; "A portable calorimeter for measuring absorbed dose in radiotherapy clinic"; Dec. 2000; Phys. Med. Biol., vol. 45; pp. 3675-3691.
Y. Morishita et al., "A standard for absorbed dose rate to water in a 60Co field using a graphite calorimeter at the national metrology institute of Japan," Radiat. Prot. Dosim. 1-9 (2012) (published E-first Sep. 5, 2012).
PCT App. No. PCT/US2018/020320; International Search Report and Written Opinion dated Jul. 24, 2018.
Nelms, Benjamin et al.; "Evalution of a Fast Method of EPID-based Dosimetry for Intensity-modulated Radiation Therapy"; Journal of Applied Clinical Medical Physics, Jan. 1, 2010, pp. 140-157, XP055476020.

\* cited by examiner

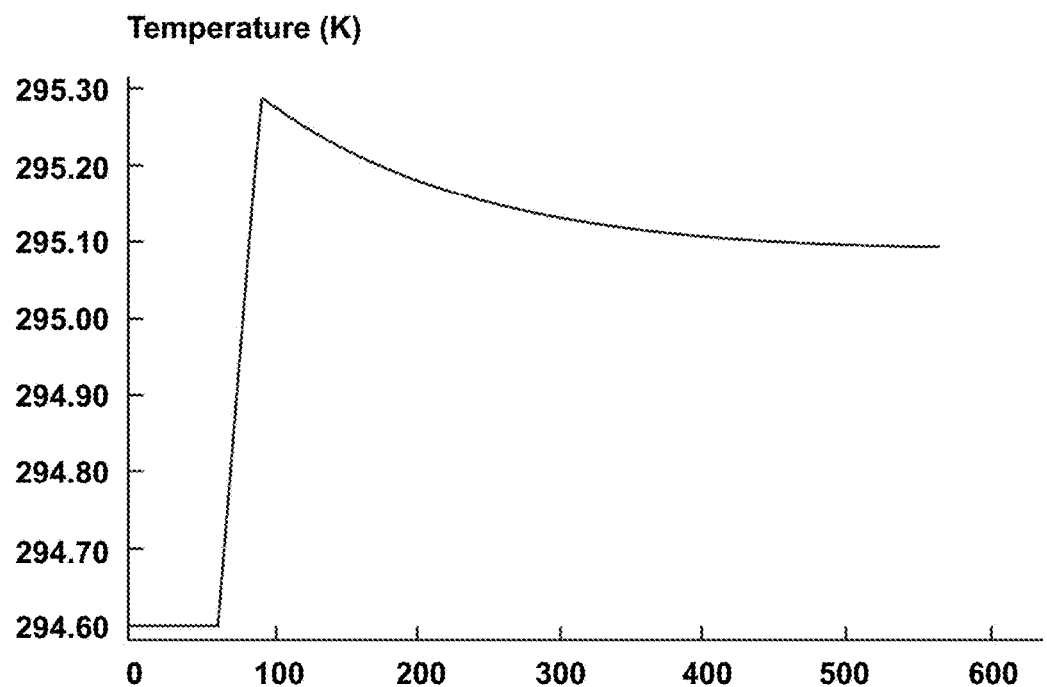
FIG. 1C
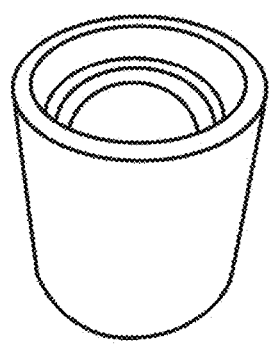 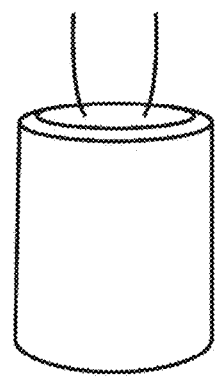
FIG. 2A        FIG. 2B

METHOD AND SYSTEM FOR CALORIMETRY PROBE

CROSS-REFERENCE TO RELATED APPLICATIONS

This patent application claims the benefit under 35 U.S.C. § 120 of U.S. patent application U.S. Ser. No. 15/448,483, filed Mar. 2, 2017 entitled "Method and System for calorimetry Probe," which claims the benefit under 35 U.S.C. § 120 of U.S. patent application Ser. No. 14/403,416, now U.S. Pat. No. 9,586,060 filed Nov. 24, 2014 entitled "Method and System for calorimetry and Clinical Dosimetry," which claims the benefit under 35 U.S.C. § 365(c) to U.S. Patent Application PCT/CA2013/000523 filed May 29, 2013 entitled "Method and System for calorimetry Probe," which claims the benefit of U.S. Provisional Patent Application 61/652,540 filed May 29, 2012 entitled "Method and System for calorimetry and Clinical Dosimetry", the entire contents of which are included by reference.

FIELD OF THE INVENTION

The present invention relates to calorimeters and in particular compact graphite based radiation calorimeters.

BACKGROUND OF THE INVENTION

Radiotherapy is one of the two most effective treatments for cancer. The success of radiotherapy in curing cancer depends critically on accurate targeting and delivery of the correct radiation dose. If the dose delivered to a patient is too low then cancerous cells may survive leading to a recurrence of the cancer. If the dose delivered is too high then surrounding healthy tissue is more likely to be damaged. For example, optimal treatment of some head and neck tumours requires that the dose delivered should be within only a few percent of that prescribed. Uncertainty in patient positioning means that it is crucial for all other errors to be as small as is possible. Accurate dosimetry is therefore essential to maintain and improve patient survival rates.

Radiation dosimetry is the measurement and calculation of the absorbed dose in matter and tissue resulting from the exposure to indirect and direct ionizing radiation. It is a scientific subspecialty in the fields of health physics and medical physics that is focused on the calculation of internal (internal dosimetry) and external doses from ionizing radiation. In medical physics absorbed dose is reported in SI units of gray (Gy) where 1 Gy=1 J/kg, and in radiation protection dosimeters in units of Sieverts (Sv).

There are different ways of measuring absorbed dose from ionizing radiation. For workers who come in contact with radioactive substances or may be exposed to radiation routinely, personal dosimeters are typically employed and intended primarily for warning/notification rather than accurate determination of dose. In the United States, these dosimeters are usually thermoluminescent dosimeters (TLD) or optically stimulated luminescence (OSL) dosimeters, whilst personal dose monitors based on photographic emulsions that are sensitive to ionizing radiation are also available. In radiotherapy, such as with linear particle accelerators in external beam radiotherapy, routine accurate calibration is typically and most commonly obtained using ionization chambers. However other detectors ranging from semiconductor-based dosimeters to radiochromic films may also be used for certain applications.

Because the human body is approximately 70% water and has an overall density close to 1 $g/cm^3$, for consistency, absorbed dose measurements are normally made in and/or reported as dose to water. National standards laboratories such as US National Institute of Standards and Technology (NIST) and UK National Physical Laboratory (NPL) provide calibration factors for ionization chambers and other measurement devices that are used to convert the instrument's readout, which may be for example ionization, optical density change, current, etc., to absorbed dose to water. The standards laboratories maintain a primary standard, which is normally based on either of three techniques: calorimetry, Fricke dosimetry, or free air ionization chambers. Out of the three, calorimetry, being the measurement of temperature rises due to radiation energy being absorbed in medium, is the most direct and absolute means of determining absorbed dose and is used most commonly.

A hospital or other users subsequently send their detectors (often ionization chambers) to the laboratory, where it is exposed to a known amount of radiation (as determined using the primary standard) and in turn a calibration factor is issued to convert the instrument's reading to absorbed dose. The user may then use this calibrated detector (secondary standard) to derive calibration factors for other instruments they use (tertiary standards) or field instruments. The uncertainty on the calibration factor of a detector increases inherently with the number of steps in the chain of calibrations relating the device to the primary standard.

Today many primary standards laboratories use water- or graphite-calorimeters to maintain an absolute photon dosimetry standard. In calorimetry, the basic assumption is that all (or a known fraction) of the absorbed radiation energy appears as heat, so that the measurement of absorbed dose reduces to a measurement of a temperature change. If the absorbed dose to water is to be established, ideally the calorimetric measurements should be made using water, see for example Ross et al in "Water calorimetry for Radiation Dosimetry" (Phys. Med. Biol., Vol. 41, pp 1-29). However, due to many challenges with water calorimetry, including low signal to noise ratio and potential heat defect due to presence of impurities in water, in addition to the cumbersome nature of the device and difficulty of working with a water tank and related accessories, significant research has also been undertaken in the area of graphite calorimetry. Graphite has beneficial radiation absorption characteristics that are similar to those of water, and allows for thermally isolated segments to be machined and configured so as to permit the measurement of absorbed dose to graphite. At present due to advances in water calorimeters arising from the work of Domen, see for example "Absorbed Dose Water calorimeter" (Med. Phys., Vol. 7, pp 157-159), both graphite and water calorimeters are exploited.

However, due to their general bulkiness and long wait times with establishing thermal equilibrium water and graphite based calorimeters have been to date, within the prior art, limited to standards laboratories. Accordingly, it would be beneficial to provide clinical medical physicists with an alternative approach to ionization chambers for the calibration and quality assurance of radiation therapy equipment including standard as well as small radiation fields. It would be further beneficial for such novel clinical dosimeters to be capable of operating as self-calibrating secondary standards, which may be used routinely for measurements rather than calibration activities only.

Radiotherapy is a field subject to continuing evolution as treatment protocols, radiopharmaceuticals, and radiotherapy equipment address both the rising rates of cancer, as more people live to an old age and as mass lifestyle changes occur in the developing world such that in 2007 approximately 13% of all human deaths worldwide (7.9 million) were cancer related, and currently there are over 200 different known types of cancers. Amongst such developments is the emergence of treatment units specifically designed for stereotactic radiosurgery, wherein small targets inside the body are treated using small static or rotating radiation fields that are at times highly modulated in both intensity and/or shape. Many radiotherapy units such as GammaKnife®, CyberKnife®, TomoTherapy®, and even most conventional linear accelerator (LINAC) manufacturers Varian®, Siemens®, Elekta® now provide the capabilities of delivering extremely complex treatment deliveries based on stereotactic radiotherapy (SRT) or intensity modulated radiation therapy (IMRT) to treat a given disease site with extreme accuracy and conformality. Accordingly, with these sophisticated techniques comes the requirement for new dosimetry protocols that address absorbed dose calibration in nonstandard radiation fields wherein practices are currently lacking international standards, see for example Alfonso et al in "A New Formalism for Reference Dosimetry of Small and Non-Standard Fields" (Med. Phys., Vol. 35, pp 5179-5186). Accordingly, calorimetry could offer a more direct and accurate way of measuring absorbed dose to water in small and composite radiation fields by doing away with the need to transfer calibration factors according to the radiation beam quality of interest.

However, calorimetry is not without its challenges when considering compact field-deployable calorimeters. Graphite has a specific heat capacity one-sixth that of water and therefore for a given radiation dose, its temperature rises 6 times more than an equivalent water based calorimeter give rise to a higher signal to noise ratio. A typical dose of radiation to a human during radiotherapy treatment is approximately 1-2 Gy, which is 1-2 joules per kilogram. Accordingly, if we consider a calorimeter comprising a 1 cm³ piece of graphite, which weighs approximately 2 grams, this would therefore absorb around 2-4 mJ, which with a specific heat capacity of around 700 Jkg⁻¹ K⁻¹ equates to a temperature rise of just 1-2 mK. Accordingly, significant problems exist in insulating the graphite from the ambient clinical environment in order to measure such tiny temperature changes.

Accordingly, embodiments of the invention provide for compact graphite probe calorimeters (GPC) for absolute accurate clinical dosimetry to address the requirements of evolving radiotherapy systems and radiopharmaceutical therapies whilst providing medical radiation oncology technologists and medical physicists with compact, fast, low cost alternatives to ionization chambers for conventional radiotherapy calibration.

Other aspects and features of the present invention will become apparent to those ordinarily skilled in the art upon review of the following description of specific embodiments of the invention in conjunction with the accompanying figures.

SUMMARY OF THE INVENTION

It is an object of the present invention address limitations within the prior art relating to calorimeters and provide compact graphite based radiation calorimeters.

In accordance with an embodiment of the invention there is provided a calorimeter comprising:
a core providing a predetermined absorption cross-section to a predetermined radiation type;
a jacket surrounding the core to provide thermal isolation of the core from the ambient environment;
a first thermal barrier material disposed between the core and jacket; and
a temperature dependent resistor thermally coupled to the core.

In accordance with an embodiment of the invention there is provided a method of measuring a radiation dose comprising:
providing a calorimeter comprising:
a core providing a predetermined absorption cross-section to a predetermined radiation type;
a jacket surrounding the core to provide thermal isolation of the core from the ambient environment;
a first thermal barrier material disposed between the core and jacket; and a first temperature dependent resistor thermally coupled to the core;
measuring the temperature dependent resistor during application of a dose of radiation according to a predetermined regimen;
and determining the radiation dose in dependence upon at least the measurements of the temperature dependent resistor and a conversion factor relating to the calorimeter.

In accordance with an embodiment of the invention there is provided a method for verifying a radiotherapy regimen comprising
establishing a predetermined radiotherapy regimen;
determining with a microprocessor an expected temperature profile for a calorimeter of predetermined design exposed to the radiotherapy regimen;
measuring the temperature profile of a physical calorimeter of the predetermined design when exposed to a radiation source operating according to the predetermined radiotherapy regimen;
determining with the microprocessor a decision in dependence upon at least the expected temperature profile and measured temperature profile.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

Embodiments of the present invention will now be described, by way of example only, with reference to the attached Figures, wherein:

FIG. 1C depicts FEM heat transfer simulation results for a GPC according to an embodiment of the invention as depicted in FIGS. 1A and 1B;

FIG. 2A depicts a GPC according to an embodiment of the invention consisting of cylindrically nested components of graphite;

FIG. 2B depicts the GPC according to an embodiment of the invention in FIG. 2A with the platinum alloy thermistor leads covered by polyimide tubing and are threaded through holes in the jacket and shield caps;

DETAILED DESCRIPTION

Figure 1A:
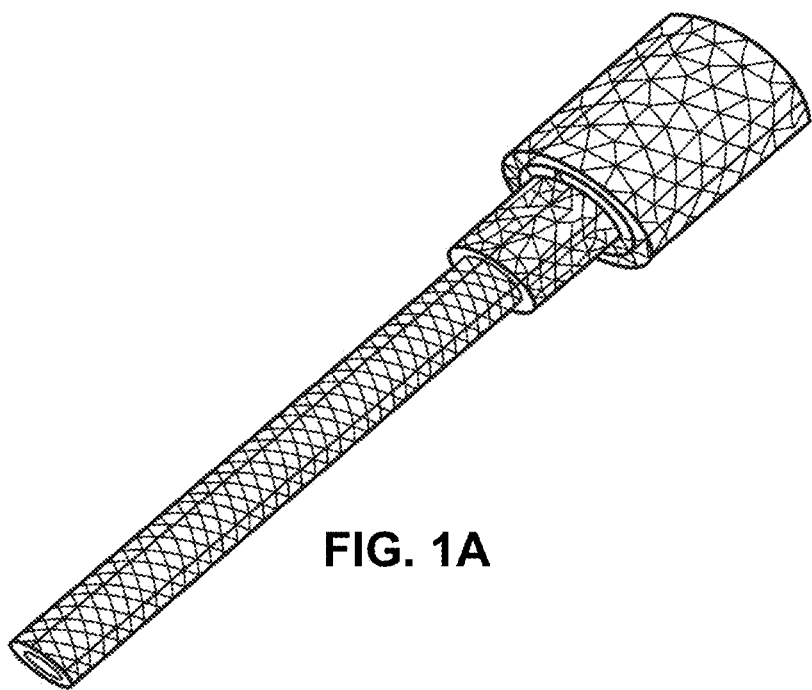
FIGS. 1A and 1B depict finite element analysis of a graphite probe calorimeter (GPC) design according to an embodiment of the invention.

The present invention is directed to calorimeters and in particular compact graphite based radiation calorimeters.

The ensuing description provides exemplary embodiment(s) only, and is not intended to limit the scope, applicability or configuration of the disclosure. Rather, the ensuing description of the exemplary embodiment(s) will provide those skilled in the art with an enabling description for implementing an exemplary embodiment. It is being understood that various changes may be made in the function and arrangement of elements without departing from the spirit and scope as set forth in the appended claims.

1. Design

A calorimeter provides a unique primary absorbed dose standard in that it does not require a radiation field for calibration. This dosimetric technique is based on the assumption that the dose, D, absorbed in a medium contributes to a temperature rise, $\Delta T$, which is proportional to the specific heat capacity, $c_p$, where $D = c_p \cdot \Delta T$. However, in practice, heat transfer, heat defects, radiation type, and radiation field perturbations due to the presence of the calorimeter are issues to consider, and potentially require consideration of corrections. Within the following description of a design and implementation for a compact, solid state calorimeter according to an embodiment of the invention a design goal of operating simultaneously for high-energy photon and electron beams was set. The photon beam being defined as x-rays from a $^{60}Co$ source up to 18 MV energy and electron beams with energies 4 MeV$\leq E_e \leq$25 MeV.

Within the embodiments of the invention described below a core design emphasis was placed on portability and ease-of-use. Accordingly, the format of the calorimeter was chosen to be probe-like, similar in size to an air-filled 0.6 $cm^3$ ionization chamber, giving it a comparable spatial resolution. The design was also intended to be robust enough to allow for repeated handling. However, these goals were subsidiary to the overarching goal of the GPC is to develop an absolute clinical dosimeter capable of providing a direct measurement of absorbed dose to water to within a sub-percent uncertainty in a practical time frame.

However, it would be evident to one skilled in the art that calorimeters according to embodiments of the invention may be designed with different design goals in terms of the radiation types, radiation energies, dosage to be measured etc. Further, other mechanical design goals may form the basis of the design in terms of volume, geometric constraints, geometry, support, and handling for example. It would also be evident that calorimeters according to embodiments of the invention may be designed for a single radiation source or multiple sources. Accordingly dosimeters according to embodiments of the invention provide increased independence on dose, dose rate, radiation energy, and energy type with appropriate design. Additionally, the embodiments of the invention describe a single graphite core but it would also be evident that embodiments of the invention may be implemented with multiple graphite cores to provide dosimetry data in respect of a predetermined physical geometry defined by an assembly housing for the multiple graphite cores or assembly into which multiple dosimeters are disposed.

1A. Mechanical Design Considerations:

The numerical design optimization study was conducted with the intent to fabricate a graphite calorimeter able to operate in the dual beams and energy ranges identified above at dose rates comparable to the range of normal LINAC operation and greater. However, embodiments of the invention operating with/without active stabilization and similar or different geometries may be employed to perform measurements at lower dose rates. Additionally, with improved response times calorimeters according to embodiments of the invention allow concurrent dose application and measurements in either continuous or pulsed approaches. With an emphasis placed on portability and easy-of-use, the format of the calorimeter was chosen to be probe-like with a target size equivalent to an air-filled 0.6 cm³ ionization chamber giving it good spatial resolution. Additionally, the design should be robust enough to allow for routine handling, for example placement within and subsequent removal from water or water-equivalent phantoms, and be able to provide a direct and reliable measurement of absorbed dose to water, with an uncertainty of 1% or better, with real time dose data and fast settling.

1B. Heat Transfer Modeling:

In quasi-adiabatic radiation mode, a graphite calorimeter measures the integrated dose-rate averaged over a graphite core volume based on its fundamental relation to temperature rise and the heat transfer, see Seuntjens et al in "Photon Absorbed Dose Standards" (Metrologia, Vol. 46, pp S39-S58), as described in Equations (1A) and (1B) where $\Delta T_{gr}$ is the temperature rise averaged over the core due to radiation, and $c_{gr,p}$ is the specific heat capacity of graphite at constant pressure.

$$\overline{D_{gr}} = c_{gr,p} \cdot \Delta T_{gr} \cdot k_{hl} \cdot \Pi k_l \quad (1A)$$

$$\overline{D_{gr}} = \frac{E_{rad}}{m_{gr}} = \frac{\Delta E_{total} - \Delta E_{transfer}}{m_{gr}} = c_{gr,p} * \Delta T_{gr} - \frac{\Delta E_{transfer}}{m_{gr}} \quad (1B)$$

Within Equation (1A) the heat loss, $k_{hl}$, is the most significant effect perturbing the measurements and hence obtaining accurate dose measurements such that the GPC optimization was primarily driven by finite element method-based numerical heat-transfer studies conducted using COMSOL Multiphysics® software. The product $\Pi k_i$ corrects for lesser effects which may be included or excluded such as in the proof of principle simulations and design analysis described below in respect of embodiments of the invention. Such effects include, but are not limited to, the presence of impurities in the graphite (which has been assumed to be small for a GPC of the target 0.6 cm³ volume described below but may not be negligible for other GPC designs), and the volume averaging effect of the graphite core. Accordingly, Equation (1B) represents a simplification such that the single correction term, $E_{transfer}/m_{gr}$, accounts for the effects of heat transfer from the core and is defined as the difference between the ideal temperature rise, in the absence of heat transfer processes, and the actual temperature rise. In calorimetry, a temperature rise is traditionally determined by linearly fitting the pre- and post-irradiation temperature traces, extrapolating them to the midpoint of the irradiation period and measuring the difference in temperature, see Seuntjens et al in "Review of calorimeter-based Absorbed Dose to Water Standards" (IAEA Int. Symp. on Standards and Codes of Practice in Med. Rad. Dosimetry, IAEA-CN-96-3).

Figure 1B:
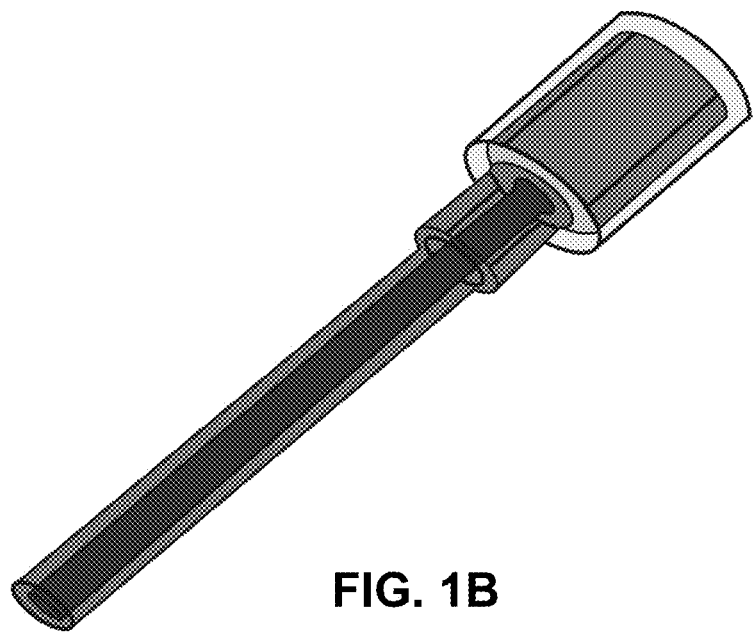

Referring to FIG. 1A there is depicted a finite element analysis meshing of a GPC according to an embodiment of the invention wherein the input parameters to the thermal simulation included thermal properties of the involved materials, boundary conditions, and the distribution of heat sources and heat sinks spatially and temporally. The resulting radiation-induced temperature distribution in a GPC according to an embodiment of the invention is depicted in FIG. 1B. Throughout the optimization process, a 2D axially-symmetric modeling of the GPC was conducted, dramatically reducing the number of mesh elements (degrees of freedom) required to describe the detector geometry. Thermistors were modeled as spheres and their power dissipation was taken into account as constant heat sources. Heat loss from the core due to conduction via the thermistor leads was also included in the model. The relative calculation tolerance was kept below 0.1% for all simulations.

For each design variation evaluated, the average temperature of the core was recorded as a function of time for the purpose of calculating a temperature rise through extrapolation of the pre- and post-irradiation traces. Such an average temperature plot for a GPC according to an embodiment of the invention being depicted in FIG. 1C from a numerical finite element method (FEM) based heat transfer study conducted using COMSOL Multiphysics™ software. Accordingly, the fast response of the GPC according to an embodiment during dosing, the linear portion of the results wherein a temperature rise of approximately 700 mK is observed within approximately 40 seconds of exposure, and the slow thermal relaxation subsequently with an approximate time constant of 120 seconds 1C. Design Optimization:

A variety of base geometries may be considered for GPC devices according to embodiments of the invention wherein different geometries may present different advantages and disadvantages in different deployment scenarios. Within this specification two GPC designs are considered: the cylinder and the sphere. The choice of shape is important as it dictates the surface area to volume ratio of the core, which in turn directly affects the amount of heat transfer experienced in a given volume. For a sphere and cylinder of common diameter, the surface area to volume ratios are the same when the length of the cylinder is equal to its diameter. Increasing the length of the cylinder decreases the surface to volume ratio, giving it an advantage over a comparable sphere. In other applications and scenarios other designs of the core may be employed including, but not limited to, spherical, cuboid, cube, triangular prism, hemisphere, hexagonal prism, pyramid, tetrahedron, octahedron, dodecahedron, and icosahedron.

Accordingly, heat simulations were conducted to determine the number and shape of the nested graphite components, namely core, jackets, and shields, to minimize the heat transfer experienced in the core. In order to narrow the design solution space, a number of constraints were imposed on the optimization process including:

the maximum diameter of the GPC was set to 20 mm;
the minimum thickness of any given graphite or insulation layer was set to 0.5 mm to keep the demands of prototype fabrication and assembly at a reasonable level;
the maximum insulation layer thickness was set to 1.0 mm so as to avoid overly large radiation field perturbation effects; and
the mass of each outer element, e.g. jacket and shield, was set to be equal to that of the absorbing core thus minimizing the magnitude of the thermal gradients across these bodies.

However, it would be evident to one skilled in the art that other design constraints may be applied according to the target GPC requirements without departing from the scope of the invention. Within the design solution space presented with respect to the GPCs within this specification insulator materials were restricted to air, polystyrene, and a flexible aerogel-based material (e.g. Pyrogel® 2250). The relevant thermal properties of these materials are listed in Table 1. Vacuum gaps were not considered for fabricating prototypes for evaluation but it would be evident to one skilled in the art that vacuum based thermal insulation may be implemented with or without an associated pumping system. It would also be evident that other materials or combination of materials to provide the required thermal barriers wherein said materials may include solid, liquids, gels, and gases. It would be further evident that where multiple additional elements surround the core, such as depicted in FIGS. 2A through 3B, 5, and 6 with the shield and jacket that the thermal barrier may be different between each sequential pair of elements.

TABLE 1

Material Properties Used in Simulating Heat Transport in COMSOL Multiphysics FEM at 22° C.

| Material | Mass Density (kgm$^{-3}$) | Specific Heat Capacity (Jkg$^{-1}$ K$^{-1}$) | Thermal Conductivity (Wm$^{-1}$ K$^{-1}$) |
|---|---|---|---|
| Pyrogel ®2250 | 170 | 1046 | 0.0155 |
| Expanded Polystyrene | 997.8 | 4.1823 | 0.6009 |
| Air | 1.194 | 1005 | 0.0259 |

Initial heat transfer simulations were aimed to determine the optimal number and shape of nested graphite components, e.g. core, jackets, shield, etc., in order to maximize the thermal isolation of the core. This was carried out using an axially-symmetric heat conduction model of the GPC, with an initial temperature set above ambient, varied between 23° C. and 40° C., was left to reach thermal equilibrium with the surrounding environment, set to 22° C. For each design variation, the average temperature of the core was traced as it decreased exponentially and the degree of thermal isolation was quantified by measuring the associated time constants. This approach was chosen because the aforementioned extrapolation method of determining temperature rises is only valid when the time scales over which temperature losses occur are much longer than the irradiation time, sec for example Seuntjens et al in "Review of calorimeter-based Absorbed Dose to Water Standards" (IAEA Int. Symp. on Standards and Codes of Practice in Med. Rad. Dosimetry, IAEA-CN-96-3).

A heat source defined in space and time to mimic the effects of the dose distribution deposited by a 6 MV photon beam was added to the heat transport model. Accurate dose distributions perturbed by the presence of inhomogeneities were calculated using Monte Carlo techniques. The dose rate $\delta D/\delta t$ for the simulated radiation source was varied between 100 cGy/min$\leq \delta D/\delta t \leq$1000 cGy/min, for irradiation times ranging between 100 seconds and 1000 seconds. Heat transfer correction factors, $k_{ht}$, were determined by measuring the ratio of the temperature rise in the core in the absence of heat transfer to that of the realistic case. The model was further refined through the addition of thermistors, platinum alloy leads, and a poly(methyl methacrylate) stem. To simulate active thermal control, a proportional, integral, derivative (PID) controller was emulated by implementing an algorithm controlling the amount of power dissipated in the shield such that a desired set point temperature is achieved and maintained.

1D. Monte Carlo Simulations:

A two-dimensional (2D) axially-symmetric model of the GPC inside a water phantom was simulated with the DOSRZnrc user code of the EGSnrcMP Monte Carlo (MC) code system, see Kawrakow et al in "The EGSnrc Code System: Monte Carlo Simulation of Electron and Photon Transport" (Canadian National Research Center, NRC Report PIRS-701, 2006). An inventor developed 6 MV photon spectrum and an electron energy cutoff of 521 keV were used. In all cases, simulations were compared to a water-only (no calorimeter present) model. A perturbation correction, $k_{gap}$, due to the presence of the aerogel (Pyrogel® 2250) was calculated, see for example Boutillon in "Gap Correction for the calorimetric Measurement of Absorbed Dose in Graphite with a $^{60}$Co Beam" (Phys. Med. Biol., Vol. 34, pp. 1809-21) and Owen et al "Correction for the Effect of the Gaps around the Core of an Absorbed Dose Graphite calorimeter in High Energy Photon Radiation" (Phys. Med. Biol., Vol. 36, pp. 1699-1704. Additionally the graphite to water absorbed dose conversion factor was calculated together with the ratio the of MC dose scored in the GPC core volume to that of an equivalent volume of water at the same depth in the absence of the detector, see for example Nutbrown et al "Evaluation of Factors to Convert Absorbed Dose Calibrations in Graphite to Water for Mega-Voltage Photon Beams" (UK National Physical Laboratory, NPL Report CIRM 37, 2000). Since both of these factors are beam-quality dependent, it would be evident that knowledge of the incident radiation spectrum is required to accurately calibrate them, and hence design simulations/design variations may therefore be required to provide the desired sensitivity/accuracy for different incident beams. The dose averaged over the volume can also be converted to absorbed dose to a point.

2. Graphite Probe Calorimeter

Figure 2C:
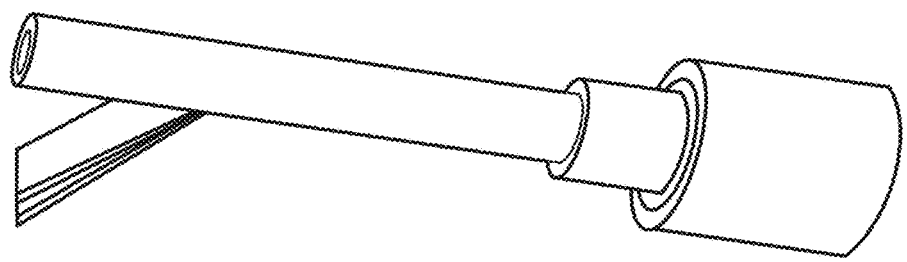
FIG. 2C depicts the GPC according to an embodiment of the invention in FIGS. 2A and 2B integrated into a PMMA stem protecting the electrical connections from the physical strain of handling and waterproofing the GPC for submerged dose measurements.

2A. Construction:

The GPC prototype according to an embodiment of the invention as depicted in FIG. 2A consists of cylindrically nested components of graphite, Grade R 4340 from SGL Carbon Group, with a density of 1.27 g/cm$^3$ with aerogel thermal insulation, Pyrogel® 2250 from Aspen Aerogels, Inc. Two negative temperature coefficient thermistors with a nominal resistance of 10 k$\Omega$ at 25° C. and a bead diameter of 0.5 mm were fixed to the core. The 6.3 mm long platinum alloy thermistor leads were covered by polyimide tubing with an inner diameter of 0.18 mm were threaded through 0.5 mm diameter holes in the jacket and shield caps allowing for electrical connections to be made to a shielded, two-lead cable outside the body, as depicted in FIG. 2B. For the jack and shield, a high purity (99%) graphite adhesive, 931 from Cotronics Corp., was used to fasten the end caps to the hollow cylinder body. A Poly(Methyl Methacrylate) (PMMA, also known as Lucite) stem was fabricated to encapsulate and waterproof the GPC for submerged dose measurements as depicted in FIG. 2C. This PMMA stem also serves as a rigid shell protecting the electrical connections from the physical strain of handling. Active thermal stabilization of the shield was not incorporated into the GPC prototype because the aim of the initial measurements was to establish a baseline of its performance, a worst case scenario, when operated in the clinical setting. However it would be evident to one skilled in the art that thermal stabilization may be implemented within a GPC according to an embodiment of the invention.

2B. Absorbed Dose Measurements:

Initial absorbed dose to water measurements made using the GPC prototype according to an embodiment of the invention were performed using a Novalis Tx radiosurgery system. The GPC was positioned horizontally inside a 30×30×6 cm$^3$ water-equivalent phantom with 1.55 cm thick water-equivalent buildup. This entire setup was placed in front of a horizontally oriented 6 MV stereotactic radiosurgery mode photon beam at 1000 MU/min dose rate and source-skin distance (SSD) of 100 cm. A field size of 10×10 cm$^2$ was used throughout the experiments. The GPC was irradiated for 12, 20, 30 and 60 seconds amounting to doses of 200, 333, 500 and 1000 monitor units (MU) respectively. Raw signals acquired were the voltage output of an active bridge type circuit. Bridge voltage was related to relative change in thermistor resistance through ohm-calibrations, see FIG. 4B, which were in turn related to a temperature rise using a thermistor calibration curve. The corresponding dose to graphite measurements were then corrected for heat transfer and radiation perturbation effects and converted to water dose using MC calculated data.

In a second series of measurements twenty-five (25) absorbed dose to water measurements were made using the GPC with the same 6 MV photon beam and Novalis Tx radiosurgery system. The GPC was positioned vertically and coincident with the central beam axis at a depth of 5.0 cm inside of a 30×30×30 cm$^3$ temperature controlled water phantom at a source-to-surface distance (SSD) of 107.3 cm. The water set-point temperature was set to 24° C. and left to stabilize overnight. Temperature control was shut-off before performing absorbed dose measurements at dose rates of 400 and 1000 MU/min. A collimator setting of 10×10 cm$^2$ was used throughout the experiments. As previously stated, raw calorimetric signals acquired were the voltage output of an active bridge type circuit, wherein such a raw calorimetric signal being depicted in FIG. 4C.

Figure 4A:
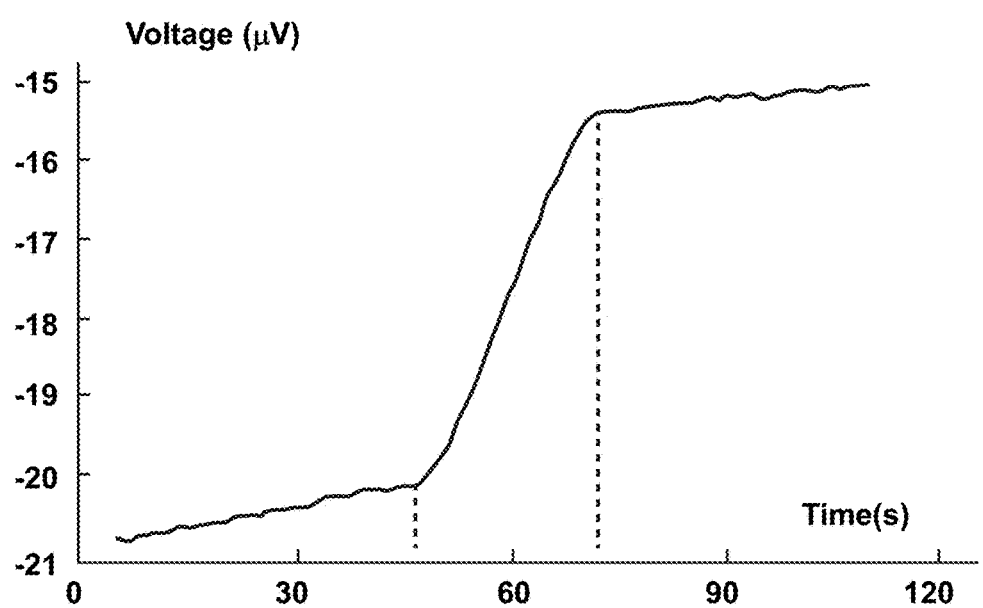
FIG. 4A depicts experimental calorimetric data in raw data from in units of active bridge voltage for the GPC according to an embodiment of the invention in FIGS. 2A through 3B acquired during a 30 s/200 MU irradiation.
Figure 4B:
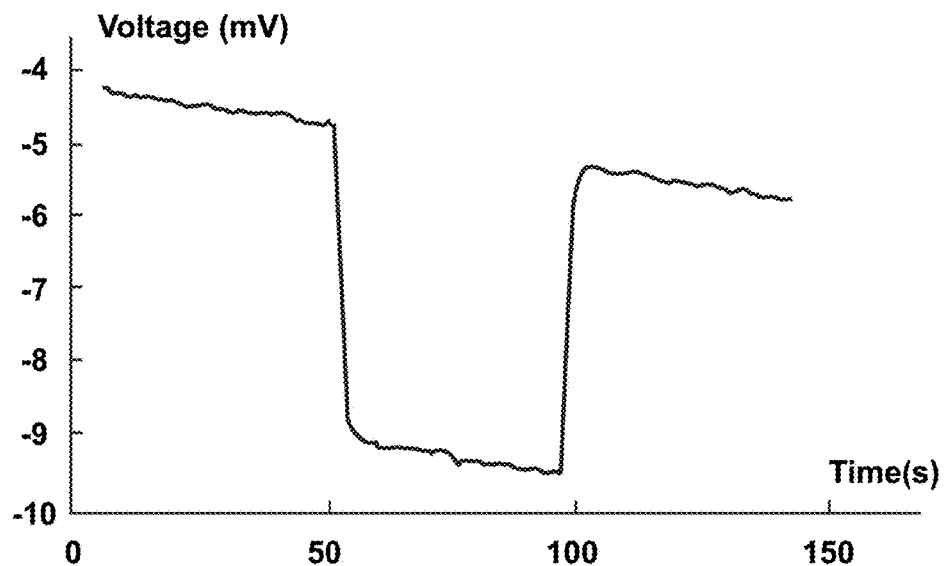
FIG. 4B depicts an ohm calibration, in which the bridge voltage response to a change in resistance of a balanced decade box by 1Ω, is recorded.
Figure 4C:
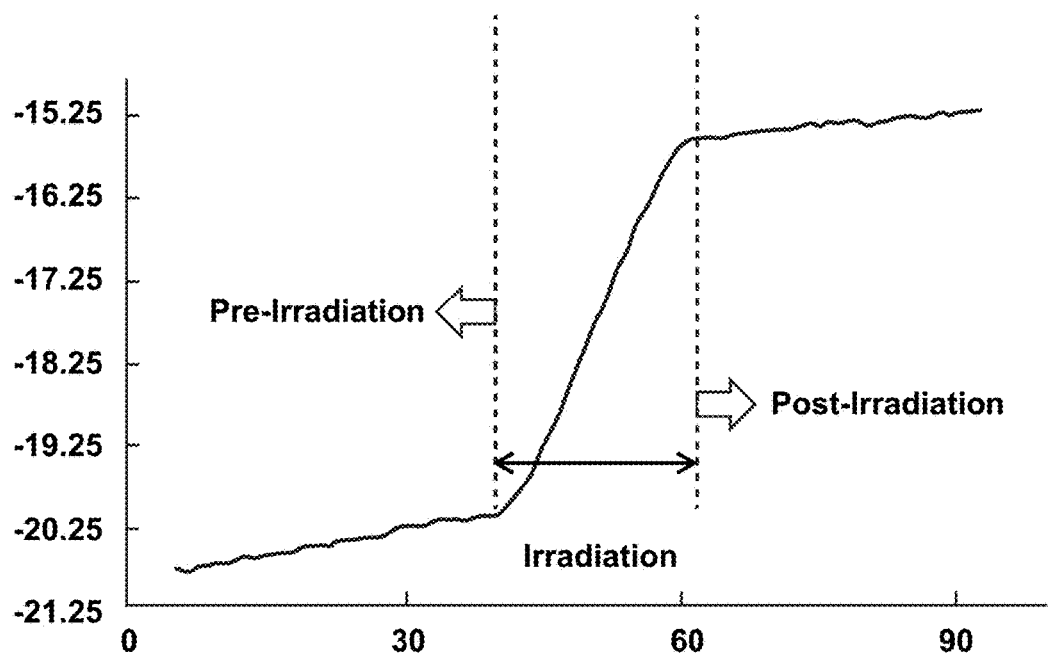
FIG. 4C depicts a raw experimental calorimetric signal for a GPC according to an embodiment of the invention in FIGS. 2A through 3B acquired during a 30 s/200 MU irradiation with the GPC within a 30×30×30 $cm^3$ water phantom.

As noted supra and depicted in FIG. 4B the bridge voltage was related to a relative change in thermistor resistance through Ohm-calibrations conducted during the experimental session. The change in thermistor resistance was in turn related to a temperature rise using a prior-measured thermistor calibration curve. The corresponding dose to graphite measurements were then corrected for heat transfer and radiation field perturbation effects and converted to water dose using MC-calculated data. GPC-acquired dose to water values were compared against dose to water measurements made with an Exradin A12 ionization chamber (Standard Imaging Inc.) with a calibration traceable to a primary standards laboratory (National Research Council of Canada), following the AAPM TG-51 protocol, see for example Almond et al in "AAPM TG-51 Protocol for Clinical Reference Dosimetry of High Energy Photon and Electron Beams" (Med. Phys., V1. 26, pp. 1847-1870).

3. Results

Figure 3A:
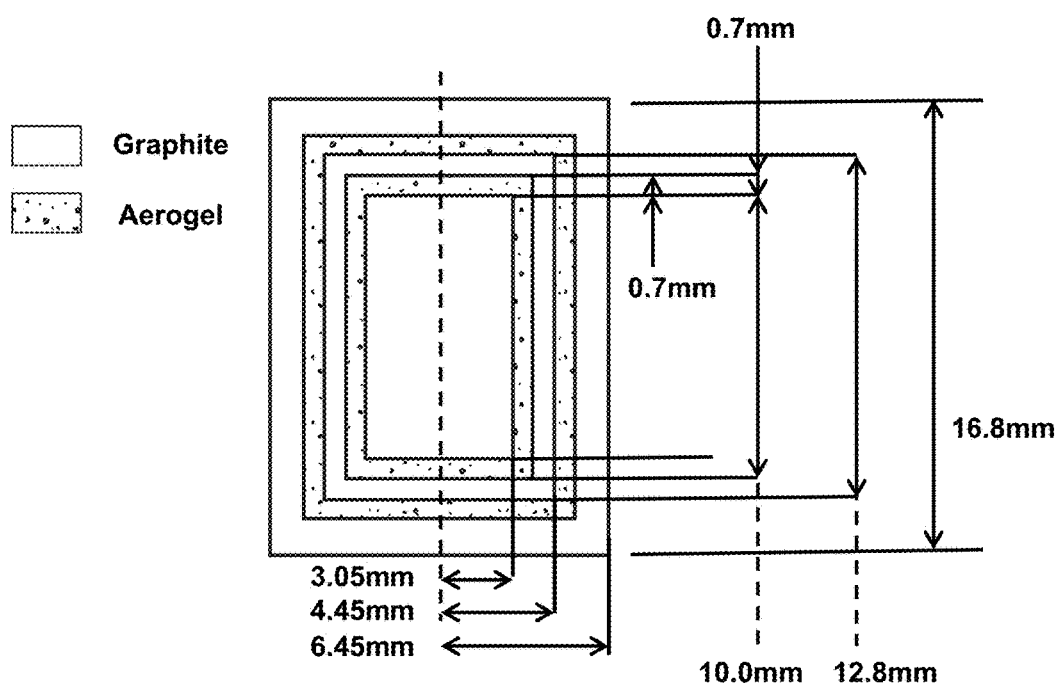
FIG. 3A depicts a schematic diagram of the GPC design of FIGS. 2A through 2B according to an embodiment of the invention.
Figure 3B:
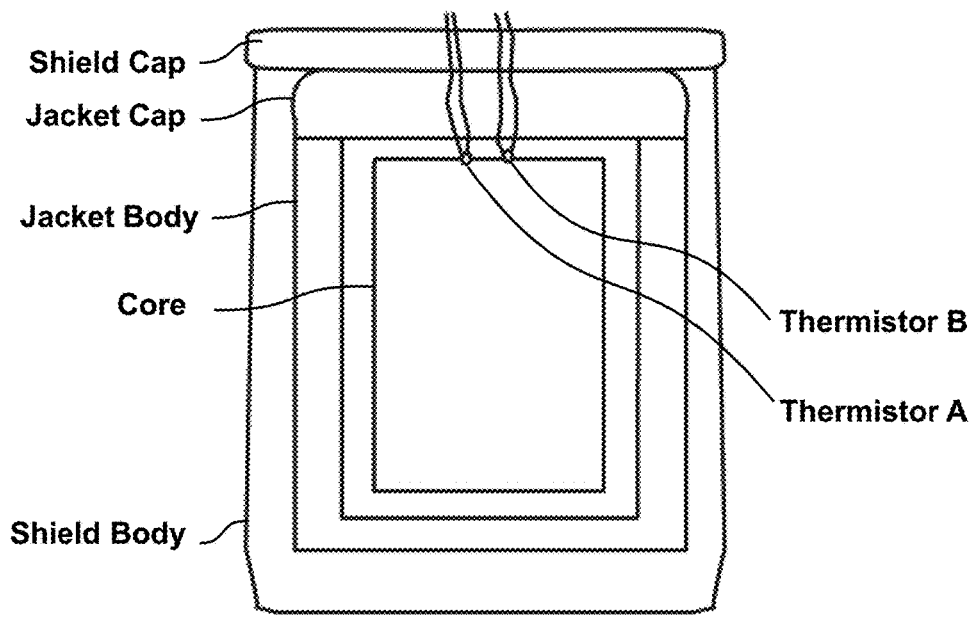
FIG. 3B depicts a microCT scan of the GPC according to the design of FIGS. 2A, 2B, and 3A according to an embodiment of the invention showing the thermistors fixed to the core.

3A. Graphite Probe calorimeter:

Referring to FIGS. 3A and 3B there are depicted a schematic diagram and X-ray microtomography (microCT) scan of the resulting GPC design as discussed above in respect of sections 1A through 1F according to an embodiment of the invention. The GPC is made up of three concentric cylinders, the first being the 6.10 mm diameter by 10.00 mm long graphite core is separated from a second 0.70 mm thick jacket cylinder by a 0.70 mm isotropic layer of insulation. Likewise, a further 1.00 mm layer of insulation thermally isolates the jacket from a 1.00 mm thick graphite shield. The aerogel was selected as the insulator due to its relatively low thermal conductivity and its ease of manipulation.

3B. Measurements: 30×30×6 cm$^3$ Water-Equivalent Phantom:

A summary of the results of initial experiments performed by delivering 200, 333, 500 and 1000 MU, at a rate of 1000 MU/min, are shown in Tables 2 and 3 below. The uncertainty in each column represents one standard deviation on those measurements. Since the calorimetric measurements were performed for different irradiation times, Table 1B also lists the calculated doses per 100 MU delivered, averaged over all measurements. The maximum absolute percent difference of measured dose to water with the GPC and that measured based on the Task Group 51 of the American Association of Physicists in Medicine (AAPM TG-51) using a tertiary reference chamber was 2.8%, a tenth of a percent larger than the estimated combined relative standard uncertainty (2.7%) of the measurements as outlined in Table 2 below. All other measurements agreed with the expected dose values within this total uncertainty.

TABLE 2

Summary of GPC Measurements for various MU Deliveries

| Delivered MU | Number of Calorimetric runs performed | Average temperature Rise (mK) | Average heat loss corrected dose to graphite (cGy) |
|---|---|---|---|
| 200 | 2 | 2.47 ± 0.01 | 178.8 ± 0.6 |
| 333 | 5 | 3.98 ± 0.03 | 287.3 ± 2.4 |
| 500 | 3 | 6.08 ± 0.01 | 437.8 ± 0.9 |
| 1000 | 2 | 11.95 ± 0.01 | 858.9 ± 1.1 |
| Total average per 100 MU | 12 | 1.21 ± 0.02 | 87.1 ± 1.2 |

TABLE 3

Summary of Dose Measurements for various MU Deliveries

| Delivered MU | Average dose to water (cGy) | TG-51 measured dose to water (cGY) | Average heat loss corrected dose to graphite (cGy) |
|---|---|---|---|
| 200 | 196.5 ± 0.7 | 193.2 | +1.7 |
| 333 | 315.8 ± 2.7 | 321.6 | −1.8 |
| 500 | 480.0 ± 1.0 | 482.9 | −0.6 |
| 1000 | 948.2 ± 1.2 | 965.8 | −1.8 |
| Total average per 100 MU | 95.7 ± 1.4 | 96.6 | −0.9 |

3C. Measurements: 30×30×30 cm$^3$ Water Phantom:

A summary of the results of the experiments performed by delivering 200 and 333 MU, at a rate of 400 and 1000 MU/min, respectively, are shown in Table 4, for the GPC disposed within the 30×30×30 cm$^3$ water phantom. The uncertainty in each column represents one standard deviation on those measurements. Table 4 also lists the averages of all quantities measured normalized to a delivery of 100 MU over the 25 measurements performed. The maximum percentage difference between a dose to water measured using the GPC and the corresponding TG-51 derived value was 2.2%. A clear trend was observed between the accuracy of dose measurement and the stability of the water bath temperature. During the first hour of measurement, the water temperature was stable to within 2 mK and the average discrepancy between the GPC and the ion chamber was 0.6%. During the last hour of measurement, the water was cooling at a rate of about 15 mK/h and the average discrepancy increased to 1.5%

TABLE 4

Dose Measurement Summary using GPC for Different MU Deliveries

| Delivered MU | Number of Calorimetric Measurements | Average Temperature Rise (mK) | Average Heat Loss Corrected Graphite (cGy) | Average Dose to Water (cGy) | TG-51 Calculated Dose to Water (cGy) | % Difference of Experiements to TG-51 |
|---|---|---|---|---|---|---|
| 333 | 20 | 2.99 ± 0.02 | 213.9 ± 1.2 | 241.8 ± 1.4 | 244.4 | +1.2 |
| 200 | 5 | 1.79 ± 0.01 | 128.1 ± 0.6 | 144.8 ± 0.6 | 145.1 | +0.2 |
| Average per 100 MU | 20 | 0.90 ± 0.01 | 64.2 ± 0.4 | 72.6 ± 0.4 | 73.2 | +0.9 |

Percentage difference in last column of Table 4 is given by Equation (2).

$$\%\text{Difference} = \frac{TG51 - \text{Calculated Dose} - \text{Measured Dose}}{TG51 - \text{Calculated Dose}} \times 100 \quad (2)$$

3D. Linearity Measurements:

Referring to Table 5 the linearity of a GPC according to an embodiment of the invention, as described supra in respect of FIGS. 1A to 3B, is presented based upon measurements using the same 30×30×30 cm$^3$ water phantom as exploited and discussed supra in respect of Section 3C. As evident from the data presented the GPC provides high linearity over dosage ranges from approximately 6 cGy to approximately 660 cGy based upon the characteristics of the design. Accordingly, it would be evident to one skilled in the art that the design of the GPC may be tailored to a particular dose range, beam profile, response rate, as well as linearity.

TABLE 5

Linearity Data for GPC using 30 × 30 × 30 cm 3 Water Phantom

| Irradiation Duration (s) | Measured Dose in Graphite (cGy) | Ratio of Dose Duration to 60 Second | Ratio of Irradiated Dose to that of 60 second Duration |
|---|---|---|---|
| 60 | 658.33 | 1 | 1 |
| 30 | 329.09 | 0.5 | 0.49989 |
| 30 | 328.89 | 0.5 | 0.49958 |
| 0.6 | 6.56 | 0.0 | 0.00996 |
| 0.06 | 0.48 | 0.001 | 0.0073 |

3E. Dose to Water Measurement Uncertainties:

In an effort to identify where the measurement differences of GPC experiments to TG-51 reference a breakdown of the estimated uncertainty budget, listing the largest contributing types A and B uncertainties used in the data analysis, was assembled. It is important to note that the uncertainty budget shown in Table 6 is meant to provide a high-level perspective and should not be considered complete but does indicate potential areas for improvement. Although the heat transfer corrections are likely to be near unity for this setup, their dependencies have not yet been fully evaluated and require a detailed sensitivity analysis. As such, this quantity has been assigned a standard uncertainty of 0.5% in accordance with the methodology of Sander, see Sander et al. in "NPL's New Absorbed Dose Standard for the Calibration of HDR$^{192}$Ir Brachytherapy Sources" (Metrologia, Vol. 49, pp. S184-S187.17). The reproducibility represents one standard deviation of the raw mean. The Ohm and thermistor calibrations reflect the uncertainty in the fits of their respective curves.

Since the specific heat capacity of the graphite used in the GPC's construction is unknown, a standard value with a rectangular distribution of 715±10 Jkg$^{-1}$ K$^{-1}$ at 24° C. was used based on the experimentally determined values using pure graphite from the literature, see for example Alberts et al. "CRC Handbook Of Chemistry and Physics" (87th Ed., CRC, Cleveland, 1976) and Picard et al in "Determination of the Specific Heat Capacity of a Graphite Sample using Absolute and Differential Methods" (Metrologia, Vol. 44, pp. 294-302). The positioning refers to the effect of the uncertainty in the GPC depth measurements. Finally, the perturbation-dose conversion refers to the statistical uncertainty in the Monte-Carlo simulations used to calculate this quantity.

On the other hand, the relative uncertainty associated with the TG-51 measurements is estimated to be 0.9% (k=1). This value was determined from the 0.7% uncertainty on the value of $N_{D,W}$ provided by the standards laboratory, 0.5% uncertainty on the beam quality conversion factor $k_Q$, see for example Rogers "The Physics of AAPM's TG-51 Protocol" (Clinical Dosimetry Measurements in Radiotherapy, Medical Physics Monograph No. 34, Medical Physics Publishing, pp. 239-298), and 0.4% total uncertainty associated with $P_{POL}$, $P_{ION}$, $P_{TP}$, humidity, depth setting, and leakage current.

TABLE 6

Estimated Uncertainty Budget for GPC in High-Energy Photon Beam Water Dose Measurements

| Quantity | Type A % uncertainty | Type B % uncertainty |
|---|---|---|
| Heat transfer correction | — | 0.5 |
| Reproducibility | 0.6 | — |
| Ohm calibration | — | 0.5 |
| Thermistor calibration | — | 0.2 |
| Specific heat capacity | — | 0.8 |
| Position | 0.2 | — |
| Perturbation-dose calibration | — | 0.4 |
| Other uncertainties not considered in this work | — | 0.4 |
| Quadratic summation | 0.6 | 1.2 |
| Combined relative standard uncertainty in dose to water | 1.4 | |

3F. Corrections and Dose Conversion:

Conductive heat transfer corrections, $k_{hl}$, calculated using a three-dimensional model of the GPC submerged in a constant temperature water phantom were determined to be 1.001 and 1.002 for the 20 s and 30 s irradiations, respectively. The effects of convection in the water phantom are assumed to be negligible. A Monte Carlo-calculated dose distribution for this experimental setup was used as a heat source input parameter in the heat transport model. The product of the radiation field perturbation factor and the graphite to water dose conversion factor was determined using MC to be 1.130±0.005.

4. Discussion

The results in Tables 2-4 demonstrate the feasibility of performing absolute clinical photon dose measurements using the GPC. The reproducibility achieved in this work is similar to the 0.6% estimated by Duane with a small-scale IMRT calorimeter, see Duane et al. in "An Absorbed Dose calorimeter for IMRT Dosimetry" (Metrologia, Vol. 49, pp. S168-S173). There are areas however, that would benefit from improvement for the devices to become routine clinical dosimeters.

As expected, the observed relation between temperature stability and measurement accuracy suggests that clinical use of the GPC will probably require it to be able to provide its own stable background temperature against which a temperature rise can be measured. The discrepancies observed between the GPC and TG-51 are partly due to the fact that the heat loss correction applied to the measured dose to graphite has been calculated assuming a stable surround temperature. In reality, the water in the tank is slowly drifting toward room temperature. As these thermal gradients increase in magnitude, the less adequate the heat transfer correction becomes. Accordingly, developing a proportional-integral-derivative (PID) temperature controller algorithm and associated electronic circuitry may be required to operate in the isothermal mode such as employed in other prior art calorimeters, see for example Daures et al in "New Constant-Temperature Operation Mode for Graphite calorimeter at LNE-LNHB" (Phys. Med. Biol., Vol. 50, pp. 4035-4052). With such a PID controller the measured quantity is the power dissipated in the core to maintain a set point temperature. Benefits of an isothermal mode include an increased reproducibility, decreased initialization time and delay time between measurements, and the ability to operate at higher dose rates than achievable when operating in the quasi-adiabatic radiation mode. Furthermore, the calibration procedure discussed supra, i.e. voltage to resistance and resistance to temperature, will become unnecessary in this mode with a priori knowledge of the core mass.

As a result, the ohm calibration (0.5%), thermistor calibration (0.2%), and specific heat capacity (0.8%) sources of type B uncertainty are replaced by the uncertainty of a mass measurement, which is expected to be no more than a few tenths of a percent. While an overall uncertainty of 1.4% was estimated for the dose measurements in this work, it is hypothesized that this can be reduced to well below 1.0% if operating in isothermal mode. With the potential for automated data analysis, the GPC could be made to be a battery-powered, absolute clinical dosimeter that could store and wirelessly transmit the measured dose values and automatically notify the user of an out-of-specification reading without anyone having to manually measure and recognize faulty values.

5. Alternate Embodiments

Accordingly, as discussed supra, isothermal mode operation may be beneficial in some embodiments of the invention. Referring to FIGS. 5A through 7B, there are depicted alternative embodiments of the invention employing resistive heating elements within different portions of the GPC together with resistive sensing elements disposed upon or within the graphite core.

Figure 5A:
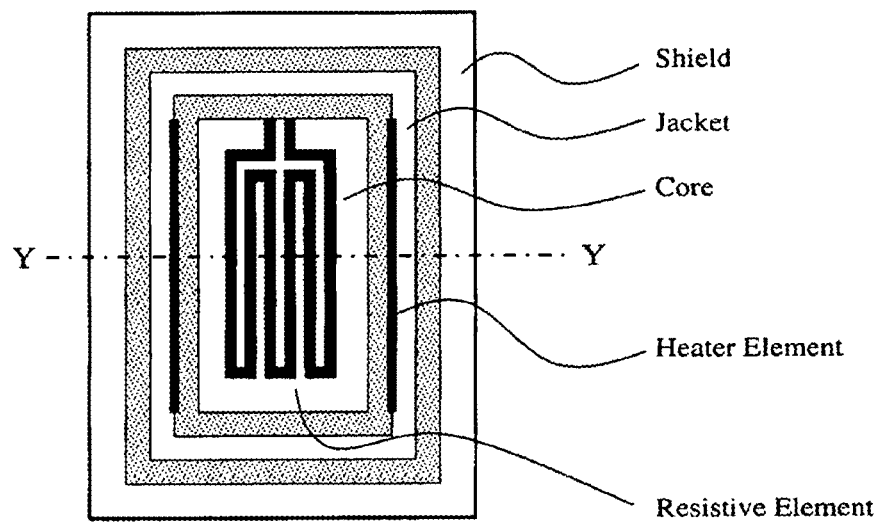
FIG. 5A depicts a GPC according to an embodiment of the invention with thin film heater and resistance elements formed upon the graphite elements.
Figure 5A:
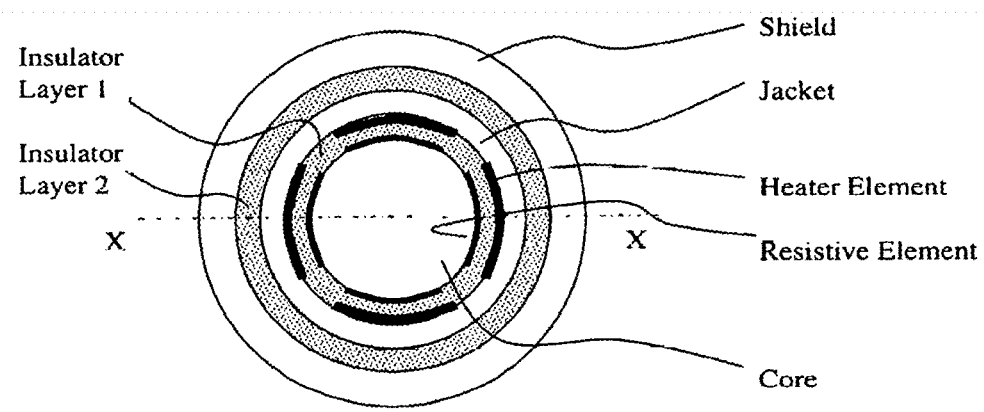

FIG. 5A depicts a circularly symmetric GPC with resistive sensor elements deposited upon the outer surface of the graphite core and resistive heating elements deposited onto the inner surface of the jacket.

Figure 5B:
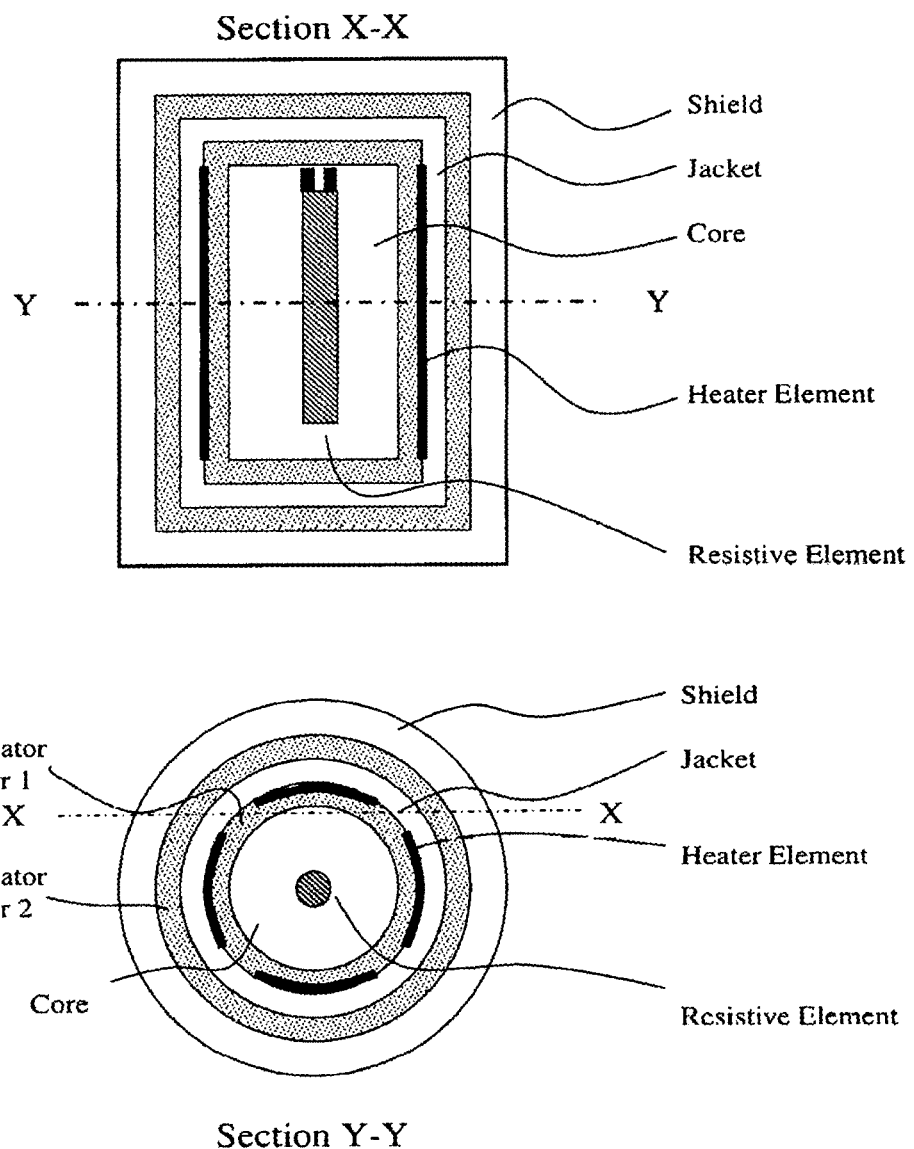
FIG. 5B depicts a GPC according to an embodiment of the invention with thin film heaters formed upon the graphite jacket and resistance element within the graphite core.

FIG. 5B depicts a circularly symmetric GPC with resistive sensor element embedded within the graphite core and resistive heating elements deposited onto the inner surface of the jacket.

Figure 5C:
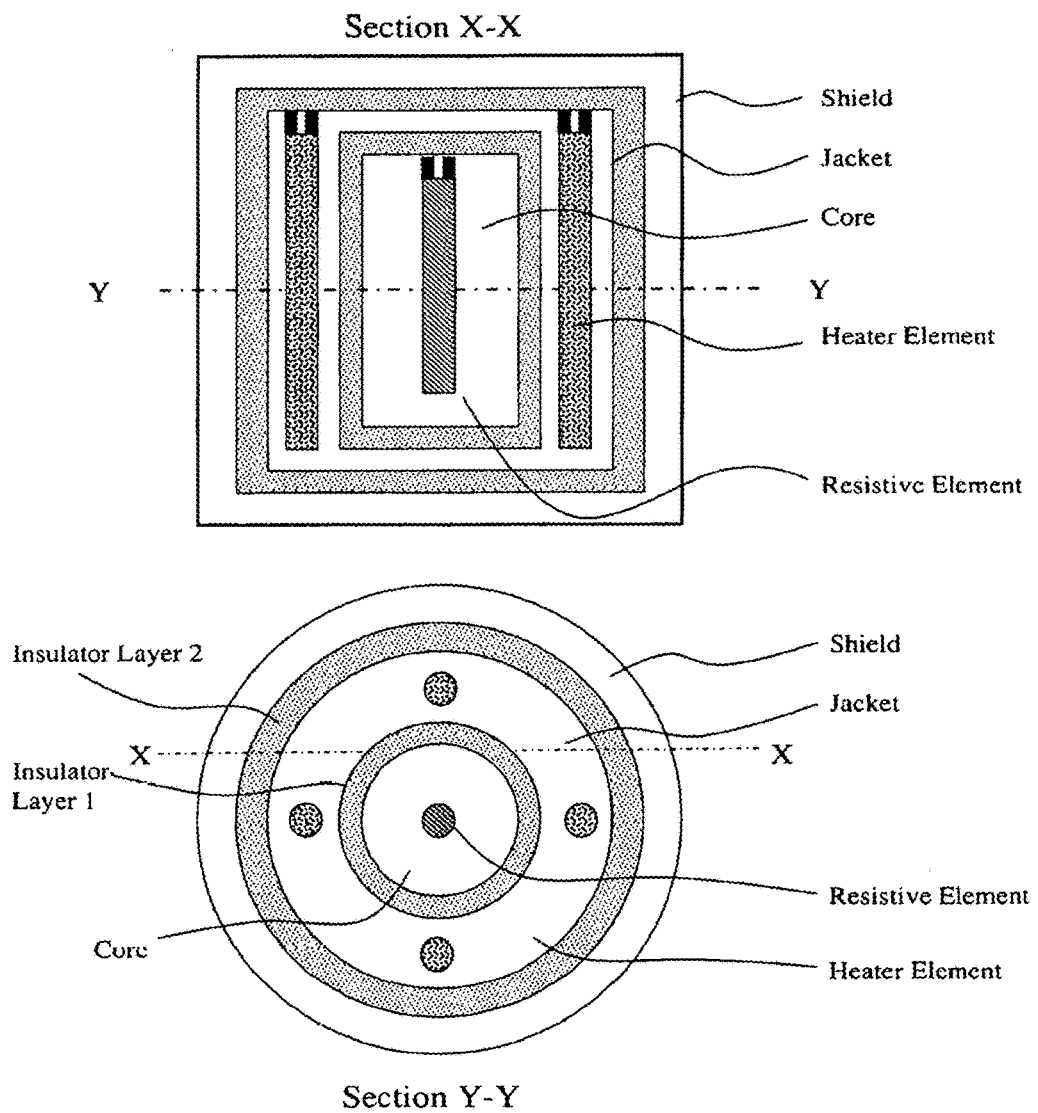
FIG. 5C depicts a GPC according to an embodiment of the invention with resistive element embedded within the graphite core and heating elements embedded within the jacket.

FIG. 5C depicts a circularly symmetric GPC with resistive sensor element embedded within the graphite core and resistive heating elements embedded within the jacket.

Figure 6:
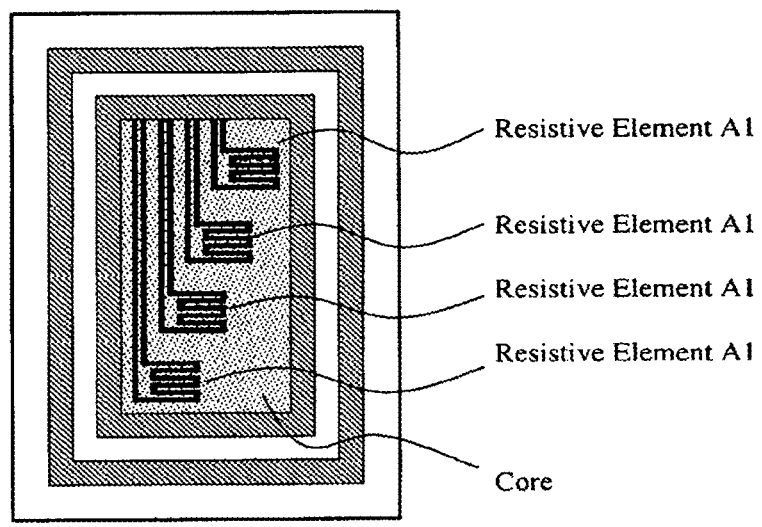
FIG. 6 depicts a GPC according to an embodiment of the invention with thin film heaters upon the graphite jacket and multiple resistance elements formed upon the graphite core.
Figure 6:
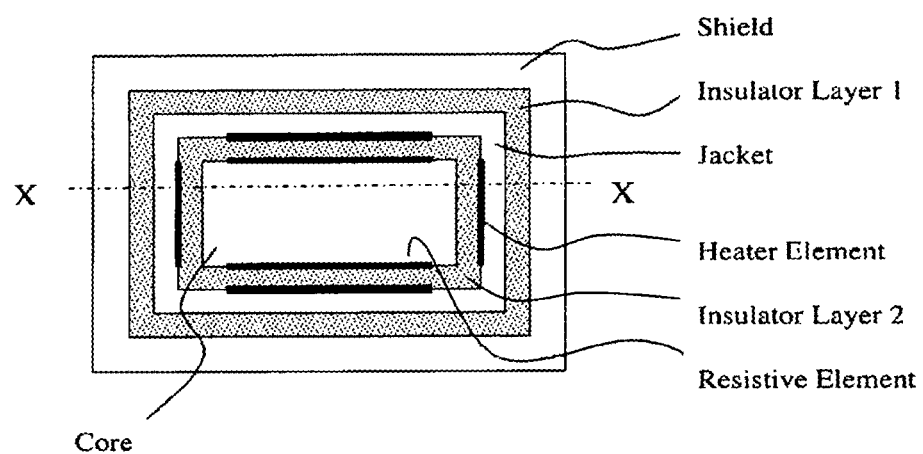

FIG. 6 depicts a rectangular GPC with multiple resistive sensor elements deposited upon the outer surface of the graphite core and heater elements are deposited onto the inner surface of the jacket.

Figure 7A:
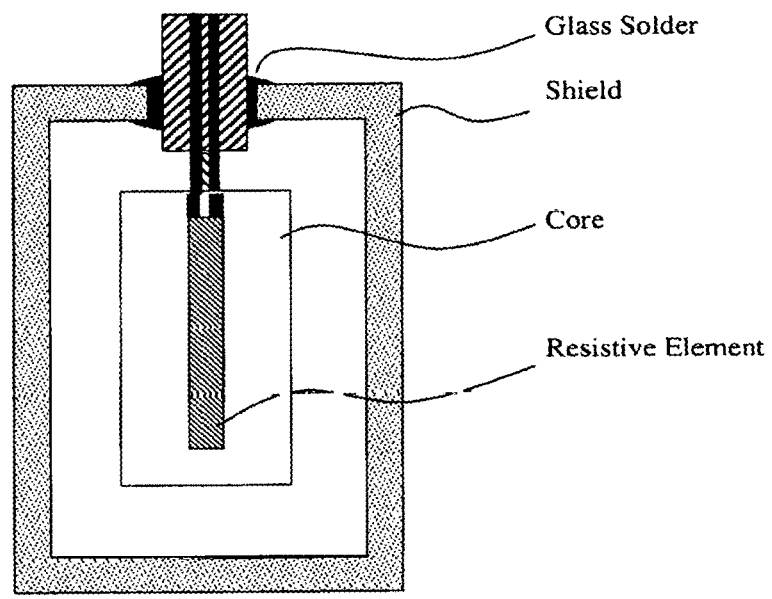
FIG. 7A depicts a GPC according to an embodiment of the invention wherein a graphite core with thin file resistance elements is sealed within a jacket under vacuum with low temperature glass based sealing.

FIG. 7A depicts a circularly symmetric GPC with resistive sensor elements embedded within the graphite core which is held within a vacuum environment formed through the sealing of a low thermal conductivity glass rod, which is attached to the graphite core, to the ceramic outer jacket using a low temperature glass frit based sealing process.

Figure 7B:
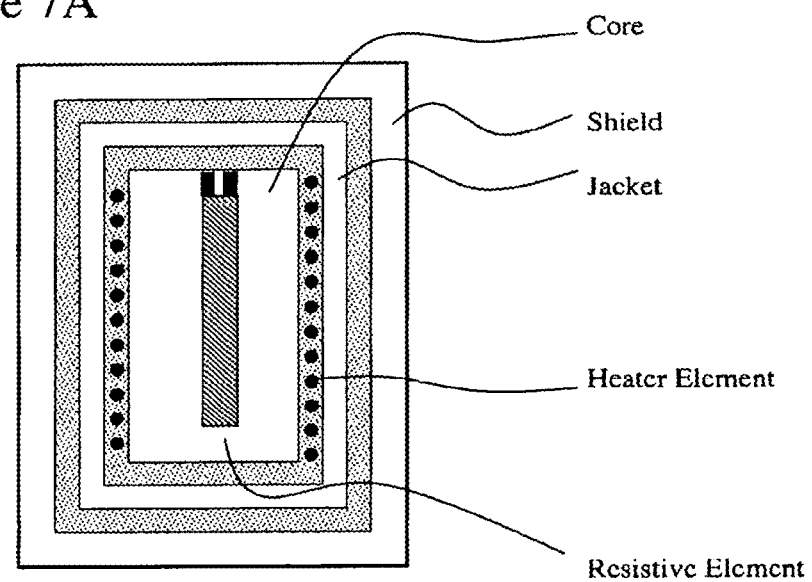
FIG. 7B depicts a GPC according to an embodiment of the invention with wire wound heaters formed around the graphite core and resistance element within the graphite core.

FIG. 7B depicts a GPC according to an embodiment of the invention with wire wound heaters formed around the graphite core and resistance element within the graphite core.

It would be evident to one skilled in the art that the temperature dependent resistive sensor elements formed on the graphic core may be thin film thermocouples formed by vacuum deposition. These foreign (non-graphite) materials may be used in amounts that do not make them affect the measurement of the principal quantity, i.e., dose to graphite. Thermocouples may employ for example nickel, iron, copper, constantan, Chromel and Alumel as metal elements. Alternatively they may be platinum or nickel resistance temperature detectors (RTDs), semiconductor thermistors, or sintered metal oxide thermistors. They may exhibit positive or negative temperature coefficients. Similarly the heater elements may be formed from metals including, but not limited to platinum, nikeline, constantan, manganin, nickel-chrome (nichrome), and copper. It would also be evident that the shield and/or jacket may be formed from other materials according to the overall thermal and mechanical design constraints. Such materials may include, but not be limited to, quartz, glass, ceramic, borosilicate glass, alumina, aluminum nitride, mullite, and beryllia. All such materials may be metalized for formation of the heating elements within the GPC. It would also be evident that according to design and manufacturing variations that temperature sensing elements may be formed within the core as well as on the outer surface of the core and that the core may be formed from multiple elements as well as a single element.

Accordingly, the jacket, and potentially the shield as well, may contain resistive heating elements, which are actively controlled to maintain a constant higher-than-ambient temperature. By maintaining a constant jacket temperature, thermal equilibrium across the encased calorimeter components will be achievable, thus minimizing heat loss from the core. While some heat transfer in the core is inevitable due to inherent dose gradients, it is expected that active thermal stabilization should sufficiently minimize this effect such that the repeatability of the radiation-induced temperature rise is improved to within a few tenths of a percent. Additionally as evident from FIG. 6 it would be evident that segmented heaters operating in conjunction with multiple thermal sensor elements on the core may provide for more complex control and feedback methods, see for example Daures. According to other embodiments of the invention, heater elements and RTD elements may be formed onto the core together such that thermal stability is achieved through one set of RTD elements providing feed-back to a thermal controller driving the heater elements before a second set of KID elements are read for the dose measurement. If a long thermal time constant exists for the GPC relative to the dose regimen being implemented then the heating circuit may be disabled for the duration of the measurement to reduce noise and control artifacts within the measurements.

Thermistor calibration in a computer-controlled variable water bath can render calibration of the device to an uncertainty of 0.2-0.3%, as has been demonstrated with thermistors used in Domen-type water calorimeters, see for example Stewart in "The Development of New Devices for Accurate Radiation Dose Measurement: A Guarded Liquid Ionization Chamber and an Electron Sealed Water calorimeter" (Ph.D. Dissertation, McGill University, 2007). In short, calibration is achieved by dissipating an accurately known amount of electrical energy into the core in the absence of radiation and measuring the resulting response of the active bridge circuit, thus directly relating energy absorbed to bridge voltage. This mode of operation has the added advantage of not requiring a priori knowledge of the specific heat capacity of the absorber medium. By developing a calibration process based on the quasi-adiabatic electrical mode of operation, the ohm-calibration, thermistor calibration and specific heat capacity sources of Type B uncertainty can be replaced by a single electrical calibration uncertainty.

Accordingly, a GPC according to embodiments of the invention could be made to be a battery-powered, self-calibrating dosimeter that could notify the user of an out-of-specification response without anyone having to manually measure faulty values. Such an integrated stand-alone GPC being depicted in FIG. 8 wherein integrated heaters and RTDs are couple to heater and RTD circuits respectively which are themselves coupled to a microprocessor controller executing a program determining feedback to the heater circuit and deriving dose measurements from the RTD measurements. This dose data may be stored within integrated memory to the microprocessor or a separate memory. Additionally the microprocessor communicates with an interface, which may for example be a wired interface such as 12C for example, or a wireless interface such as Bluetooth, allowing transfer of dose data from the GPC as well as downloading of new program data, calibration data etc. Optionally, the GPC may be used for Quality Assurance of an intended radiotherapy regimen. Accordingly the microprocessor may receive the radiotherapy regimen profile of dose versus time, measure the actual regimen and determine whether the required regimen profile was achieved or not. Optionally, the GPC may simply stream dose versus time data to a remote controller for data logging, regimen verification, etc.

Figure 8:
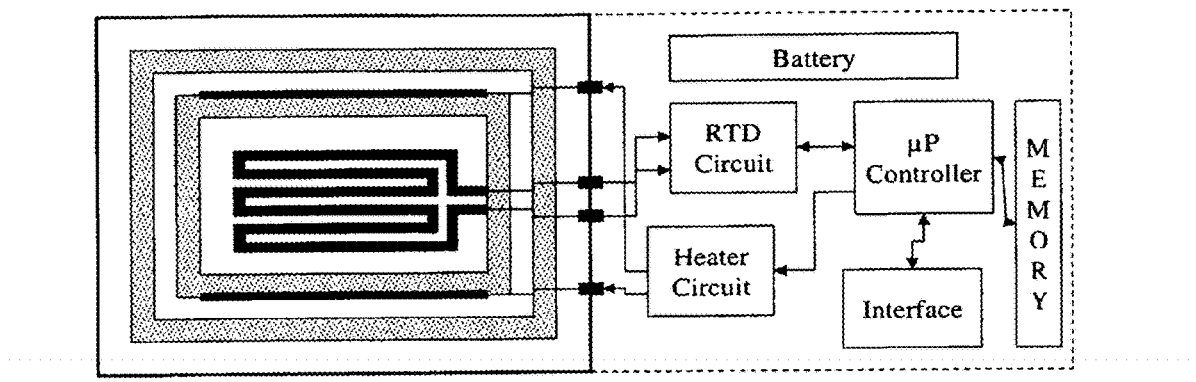
FIG. 8 depicts an integrated GPC assembly comprising a GPC according to an embodiment of the invention in conjunction with thermal control and temperature sensing electronics for a stand-alone battery operated absolute calorimeter.

It would be evident that whilst a microprocessor based controller is described in respect of FIG. 8 that alternatively designs employing field-programmable gate array (FPGA) or complex programmable logic device (CPLD) architectures are feasible. In some instances a direct RTD read circuit may be provided within an FPGA or CPLD with only a small block consumption overall within the circuit.

Figure 9:
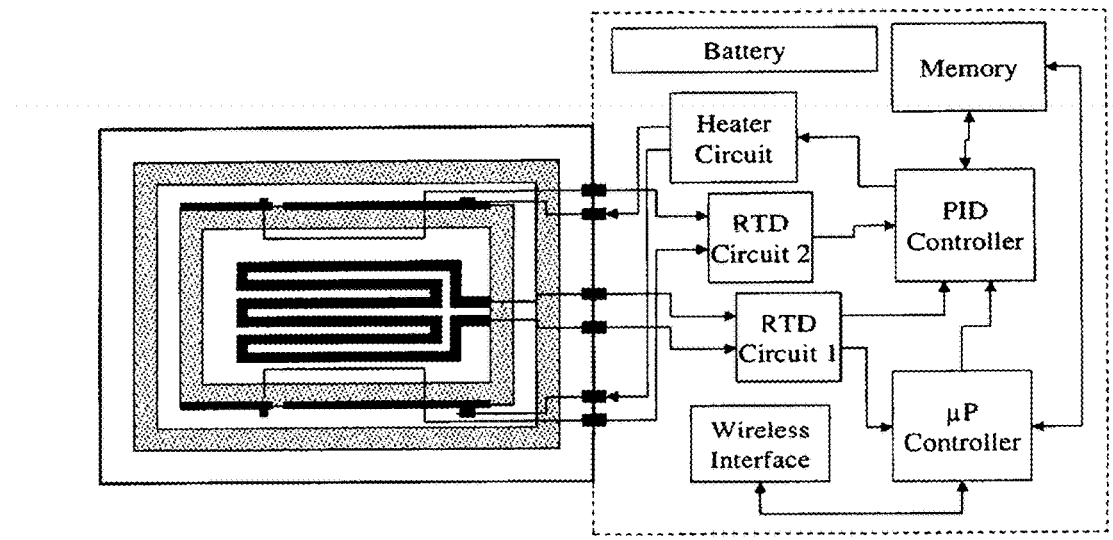
FIG. 9 depicts an integrated GPC assembly comprising a GPC according to an embodiment of the invention in conjunction with thermal control, calorimeter and jacket temperature sensing electronics for a stand-alone battery operated absolute calorimeter with wireless interface.

Alternatively an integrated GPC such as depicted in FIG. 8 may be designed for interconnection via a standard connector, e.g. micro-USB, allowing the GPC to be directly powered, c.f. USB 2.0 specification, and data logged during operation from a host computer such as a laptop or smartphone. Alternative embodiments of the invention exploiting thin-film temperature sensing elements, thin-film heaters, thick-film heaters, thermistors, RTDs, etc. may be formed with different geometries according to different mechanical and thermal constraints needs based on dose ranges, dose rate, radiation delivery type, and radiation type. Similarly, as depicted in FIG. 9 an integrated GPC may be designed to be self-contained with a battery and supporting a wireless interface, such as for example Bluetooth, IEEE 802.11, IEEE 802.15, Zigbee, and Wireless USB allowing the integrated GPC to automatically connect to a local area network or personal area network to communicate all dose measurements or only those that fall outside a predetermined range programmed into the GPC controller. Such integrated GPC's may be charged/recharged through the standard connector in the design depicted in FIG. 8 or through a wireless/inductive interface in addition to the one supporting data communications such as depicted in FIG. 9. It would also be evident that the integrated GPC may store multiple measurements prior to their transmission via a wired/wireless interface. Further, in FIG. 9 a dedicated PID Controller interfaces with the heater circuit with feedback from first and second RTD circuits, one coupled to the RTD within the graphite core and the other coupled to RTDs on the inner surface of the shield upon which the heaters are also disposed. As discussed supra multiple heater elements and RTDs for example may be employed in conjunction with each other to provide distributed heating, temperature feedback, and temperature sensing for dose measurement.

Figure 10:
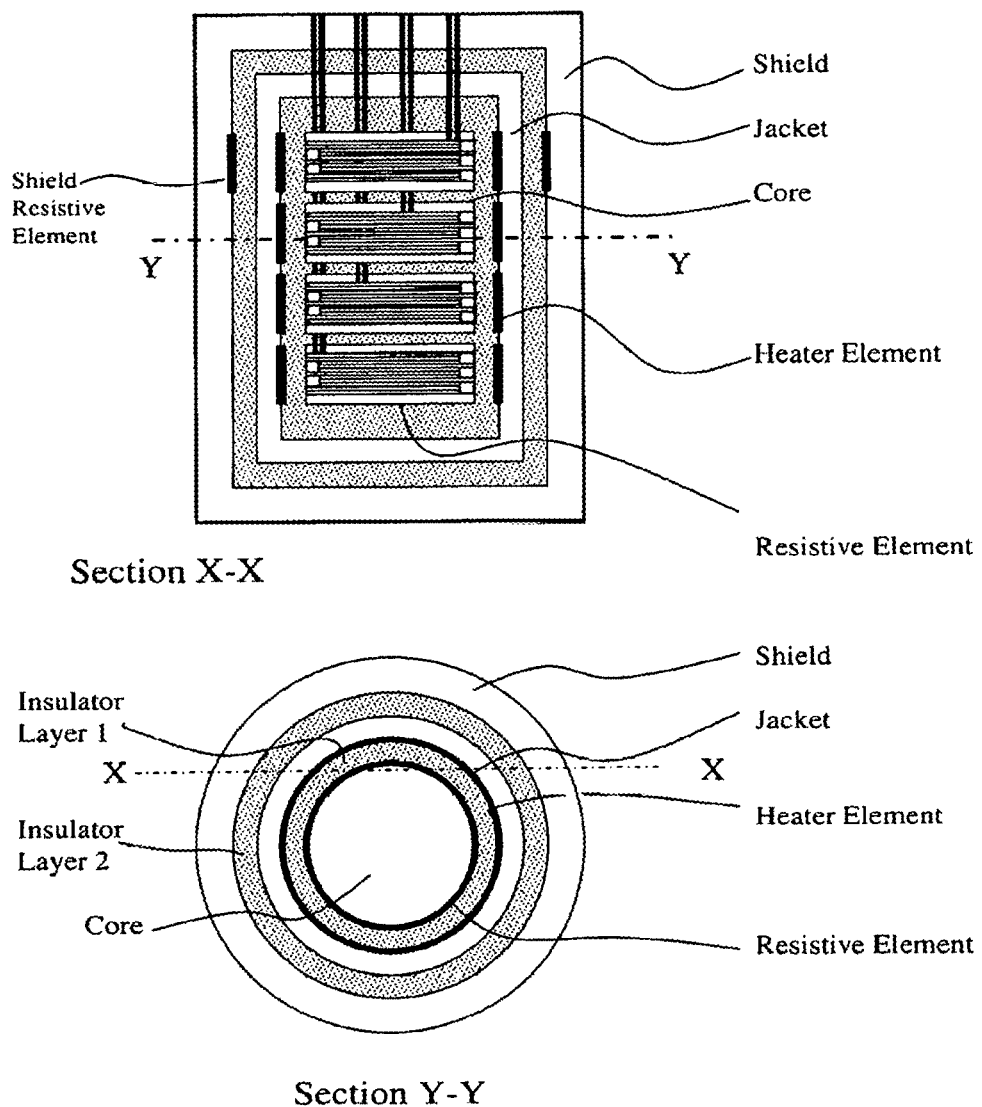
FIG. 10 depicts a GPC according to an embodiment of the invention with multiple graphite cores with wire wound heaters formed around each core, with core specific temperature sensors and jacket heating elements segmented to align with each graphite core.

Alternatively, as depicted in FIG. 10 multiple graphite cores may be disposed within a common jacket and shield, in this instance vertically although horizontally and/or 3D arrays may be also implemented. Each graphite core has disposed, in this instance, a resistive element upon the outer surface to provide temperature measurement (although as discussed supra other configurations may be employed together with others not presented in Figures). Additionally, multiple heater elements are disposed on the inner surface of the jacket, as opposed to a single heater element, aligned with each graphite core such that adjustment of graphite core's via said heaters may be controlled together, individually, in associated groups, or multiple associated groups wherein a single heater may for example be associated with 2 or more groups (e.g. the third heater in a linear array may be associated with element groups (1,2,3); (2,3,4); and (3,4,5). Also disposed on the inner surface of the shield is a shield resistive element providing temperature dependent resistance data to a PID controller, heater controller, microprocessor, or other control system.

Within the preceding discussions in respect of embodiments of the invention and in respect of FIGS. 1A through 10 temperature sensing elements within the various embodiments have been described primarily on the basis that these are resistive structures, i.e. having resistance R. However, it would be evident to one skilled in the art that these may alternatively be capacitive with capacitance C, inductive with inductance L, LC circuits, or RLC circuits such that, for example, the frequency offset of a resonant circuit with temperature or impedance with temperature may form the basis for temperature measurement. In some embodiments of the invention, such as a spiral inductor, an external antenna may be used to electromagnetically excite the spiral inductor wherein the impedance variations of the external antenna exciting the spiral inductor will depend upon the temperature of the spiral inductor. Accordingly, the graphite core may be embedded within an insulator without any external connection for temperature sensing.

Specific details are given in the above description to provide a thorough understanding of the embodiments.

However, it is understood that the embodiments may be practiced without these specific details. For example, circuits may be shown in block diagrams in order not to obscure the embodiments in unnecessary detail. In other instances, well-known circuits, processes, algorithms, structures, and techniques may be shown without unnecessary detail in order to avoid obscuring the embodiments.

The foregoing disclosure of the exemplary embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

What is claimed is:

1. A calorimeter comprising:
   a plurality of cores;
   a jacket surrounding the plurality of cores to provide thermal isolation of the plurality of cores from the ambient environment;
   a thermal barrier between the plurality of cores and the jacket; and
   a temperature sensing element thermally coupled to each of the cores.

2. The calorimeter according to claim 1, wherein the calorimeter has a volume of approximately 0.6 $cm^3$.

3. The calorimeter according to claim 1, wherein the calorimeter has a volume of approximately 14 $cm^3$.

4. The calorimeter according to claim 1, wherein the calorimeter has a volume less than or equal to 0.6 $cm^3$.

5. The calorimeter according to claim 1, wherein the calorimeter has a volume less than or equal to 14 $cm^3$.

6. The calorimeter according to claim 1, wherein the plurality of cores has a volume of approximately 0.3 $cm^3$.

7. The calorimeter according to claim 1, wherein the plurality of cores has a volume less than or equal to 0.3 $cm^3$.

8. The calorimeter according to claim 1, wherein each of the plurality of cores has a diameter of approximately 6 mm.

9. The calorimeter according to claim 1, wherein each of the plurality of cores has a diameter of less than or equal to 6 mm.

10. The calorimeter according to claim 1, wherein the calorimeter has a diameter of approximately 13 mm.

11. The calorimeter according to claim 1, wherein the calorimeter has a diameter of less than or equal to 13 mm.

12. The calorimeter according to claim 1, wherein the plurality of cores are vertically disposed within the jacket.

13. The calorimeter according to claim 1, wherein the plurality of cores are horizontally disposed within the jacket.

14. The calorimeter according to claim 1, further comprising:
   a microprocessor coupled to the temperature sensing element; and
   a wireless interface,
   wherein the microprocessor is configured to derive dose data from temperature sensing element measurements and the wireless transmitter is configured to transfer the dose data from the calorimeter.

15. The calorimeter according to claim 1, wherein the maximum diameter of the calorimeter is 20 mm.

* * * * *